(12) United States Patent
Neumann

(10) Patent No.: US 12,112,244 B2
(45) Date of Patent: Oct. 8, 2024

(54) SYSTEM AND METHOD FOR GENERATING A PROCREANT FUNCTIONAL PROGRAM

(71) Applicant: KPN INNOVATIONS, LLC., Lakewood, CO (US)

(72) Inventor: Kenneth Neumann, Lakewood, CO (US)

(*) Notice: Subject to any disclaimer, the term of this patent is extended or adjusted under 35 U.S.C. 154(b) by 812 days.

(21) Appl. No.: 17/221,384

(22) Filed: Apr. 2, 2021

(65) Prior Publication Data
US 2022/0207423 A1    Jun. 30, 2022

Related U.S. Application Data

(63) Continuation-in-part of application No. 17/136,199, filed on Dec. 29, 2020, now Pat. No. 11,049,603.

(51) Int. Cl.
*G06N 20/00* (2019.01)
*A61B 5/00* (2006.01)
(Continued)

(52) U.S. Cl.
CPC ........... *G06N 20/00* (2019.01); *A61B 5/43* (2013.01); *G16H 10/40* (2018.01); *G16H 10/60* (2018.01); *G16H 20/00* (2018.01)

(58) Field of Classification Search
None
See application file for complete search history.

(56) References Cited

U.S. PATENT DOCUMENTS 7,074,183 B2    7/2006  Castellanos
7,970,620 B2    6/2011  Brown
(Continued)

FOREIGN PATENT DOCUMENTS

RU     2691145 C2    6/2019
WO    2014015378      1/2014
(Continued)

OTHER PUBLICATIONS

Verma M, Hontecillas R, Tubau-Juni N, Abedi V, Bassaganya-Riera J. Challenges in Personalized Nutrition and Health. Front Nutr. Nov. 29, 2018;5:117. doi: 10.3389/fnut.2018.00117. PMID: 30555829; PMCID: PMC6281760. (Year: 2018).*

(Continued)

*Primary Examiner* — Devin C Hein
(74) *Attorney, Agent, or Firm* — Caldwell Intellectual Property Law

(57) ABSTRACT

A system for generating a procreant functional program includes a computing device configured to obtain a procreant marker as a function of a procreant system, determine a procreant appraisal as a function of the procreant marker, wherein determining further comprises producing a procreant enumeration as a function of the procreant marker, and determining the procreant appraisal as a function of the procreant enumeration, and a safe range, receive a conduct indicator, identify a functional signature as a function of the conduct indicator, wherein identifying further comprises obtaining a salubrious reference, and identifying the functional signature as a function of the salubrious reference and the conduct indicator using a functional machine-learning model, and generate a functional program as a function of the functional signature and procreant appraisal using a program machine-learning model.

20 Claims, 10 Drawing Sheets

(51) Int. Cl.
  *G16H 10/40* (2018.01)
  *G16H 10/60* (2018.01)
  *G16H 20/00* (2018.01)

(56) References Cited

U.S. PATENT DOCUMENTS

| | | | |
|---|---|---|---|
| 8,226,414 B2 | 7/2012 | Bodin | |
| 8,560,336 B2 | 10/2013 | Schwarzberg | |
| 8,684,922 B2 | 4/2014 | Tran | |
| 10,373,522 B2 | 8/2019 | Byron | |
| 2002/0046060 A1 | 4/2002 | Hoskyns | |
| 2006/0074279 A1 | 4/2006 | Brover | |
| 2006/0199155 A1 | 9/2006 | Mosher | |
| 2010/0042438 A1 | 2/2010 | Moore | |
| 2010/0070455 A1 | 3/2010 | Halperin | |
| 2010/0136508 A1 | 6/2010 | Zekhtser | |
| 2013/0261183 A1 | 10/2013 | Bhagat | |
| 2014/0255882 A1* | 9/2014 | Hadad | G09B 19/0092 434/127 |
| 2014/0310019 A1* | 10/2014 | Blander | G16H 40/67 705/2 |
| 2015/0088541 A1* | 3/2015 | Yao | G06Q 10/10 705/2 |
| 2015/0161355 A1 | 6/2015 | Karra | |
| 2015/0356885 A1 | 12/2015 | Chen | |
| 2016/0225284 A1 | 8/2016 | Schoen | |
| 2018/0308389 A1 | 10/2018 | Moser | |
| 2019/0027232 A1* | 1/2019 | Beim | G16B 50/20 |
| 2019/0074080 A1 | 3/2019 | Appelbaum | |
| 2019/0078142 A1* | 3/2019 | Apte | G16B 20/00 |
| 2019/0221303 A1 | 7/2019 | Bennett | |
| 2019/0251861 A1 | 8/2019 | Wolf | |
| 2020/0138362 A1 | 5/2020 | Koumpan | |

FOREIGN PATENT DOCUMENTS

| | | |
|---|---|---|
| WO | 2019054737 | 3/2019 |
| WO | 2019110412 | 6/2019 |
| WO | 2019229753 | 12/2019 |

OTHER PUBLICATIONS

Wang R, Pan W, Jin L, Li Y, Geng Y, Gao C, Chen G, Wang H, Ma D, Liao S. Artificial intelligence in reproductive medicine. Reproduction. Oct. 2019;158(4):R139-R154. doi: 10.1530/REP-18-0523. PMID: 30970326; PMCID: PMC6733338. (Year: 2019).*

A. M. Oprescu, G. Miro-amarante, L. García-Díaz, L. M. Beltrán, V. E. Rey and M. Romero-Ternero, "Artificial Intelligence in Pregnancy: A Scoping Review," in IEEE Access, vol. 8, pp. 181450-181484, 2020, doi: 10.1109/ACCESS.2020.3028333 (Year: 2020).*

Title: A Brief Tool to Assess Image-Based Dietary Records and Guide Nutrition Counselling Among Pregnant Women: An Evaluation; JMIR Mhealth and Uhealth vol. 4 Issue: 4 Article No. e123 Published: Oct.-Dec. 2016; By: Ashman.

Title: Biomarkers of Nutrition and Health: New Tools for New Approaches; Nutrients vol. 11 Issue: 5 Article No. 1092 Published: May 2019; By: Pico, Catalina.

Title: Role of Personalized Nutrition in Chronic-Degenerative Diseases; Nutrients vol. 11 Issue: 8 Article No. 1707 Published: Aug. 2019 DOI: 10.3390/nu11081707; By: Di Renzo, Laura.

* cited by examiner

SYSTEM AND METHOD FOR GENERATING A PROCREANT FUNCTIONAL PROGRAM

CROSS-REFERENCE TO RELATED APPLICATIONS

This application is a continuation-in-part of Non-provisional application Ser. No. 17/136,199 filed on Dec. 29, 2020 and entitled "SYSTEM AND METHOD FOR GENERATING A PROCREANT NOURISHMENT PROGRAM," the entirety of which is incorporated herein by reference.

FIELD OF THE INVENTION

The present invention generally relates to the field of artificial intelligence. In particular, the present invention is directed to a system and method for generating a procreant functional program.

BACKGROUND

Current holistic suggestion systems do not account for the procreant system of an individual. This leads to inefficiency of a holistic suggestion system and a poor outcome plan for the individual. This is further complicated by a lack of uniformity of outcome plans, which results in dissatisfaction of individuals.

SUMMARY OF THE DISCLOSURE

In an aspect, a system for generating a procreant functional program includes a computing device configured to obtain a procreant marker as a function of a procreant system, determine a procreant appraisal as a function of the procreant marker, wherein determining further comprises producing a procreant enumeration as a function of the procreant marker, and determining the procreant appraisal as a function of the procreant enumeration, and a safe range, receive a conduct indicator, identify a functional signature as a function of the conduct indicator, wherein identifying further comprises obtaining a salubrious reference, and identifying the functional signature as a function of the salubrious reference and the conduct indicator using a functional machine-learning model, and generate a functional program as a function of the functional signature and procreant appraisal using a program machine-learning model.

In another aspect, a method for generating a procreant functional program includes obtaining, by a computing device, a procreant marker as a function of a procreant system, determining, by the computing device, a procreant appraisal as a function of the procreant marker, wherein determining further comprises producing a procreant enumeration as a function of the procreant marker, and determining the procreant appraisal as a function of the procreant enumeration, and a safe range, receiving, by the computing device, a conduct indicator, identifying, by the computing device, a functional signature as a function of the conduct indicator, wherein identifying further comprises obtaining a salubrious reference, and identifying the functional signature as a function of the salubrious reference and the conduct indicator using a functional machine-learning model, and generating, by the computing device, a functional program as a function of the functional signature and procreant appraisal using a program machine-learning model.

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a procreant functional program. In an embodiment, the disclosure may obtain a procreant marker as a function of a procreant system. Aspects of the present disclosure can be used to determine a procreant appraisal as a function of the procreant marker. Aspects of the present disclosure can also be used to identify a functional signature as a function of the procreant appraisal. This is so, at least in part, because the disclosure utilizes a functional machine-learning model. Aspects of the present disclosure allow for generating a functional program as a function of the functional signature. Exemplary embodiments illustrating aspects of the present disclosure are described below in the context of several specific examples.

Figure 1:
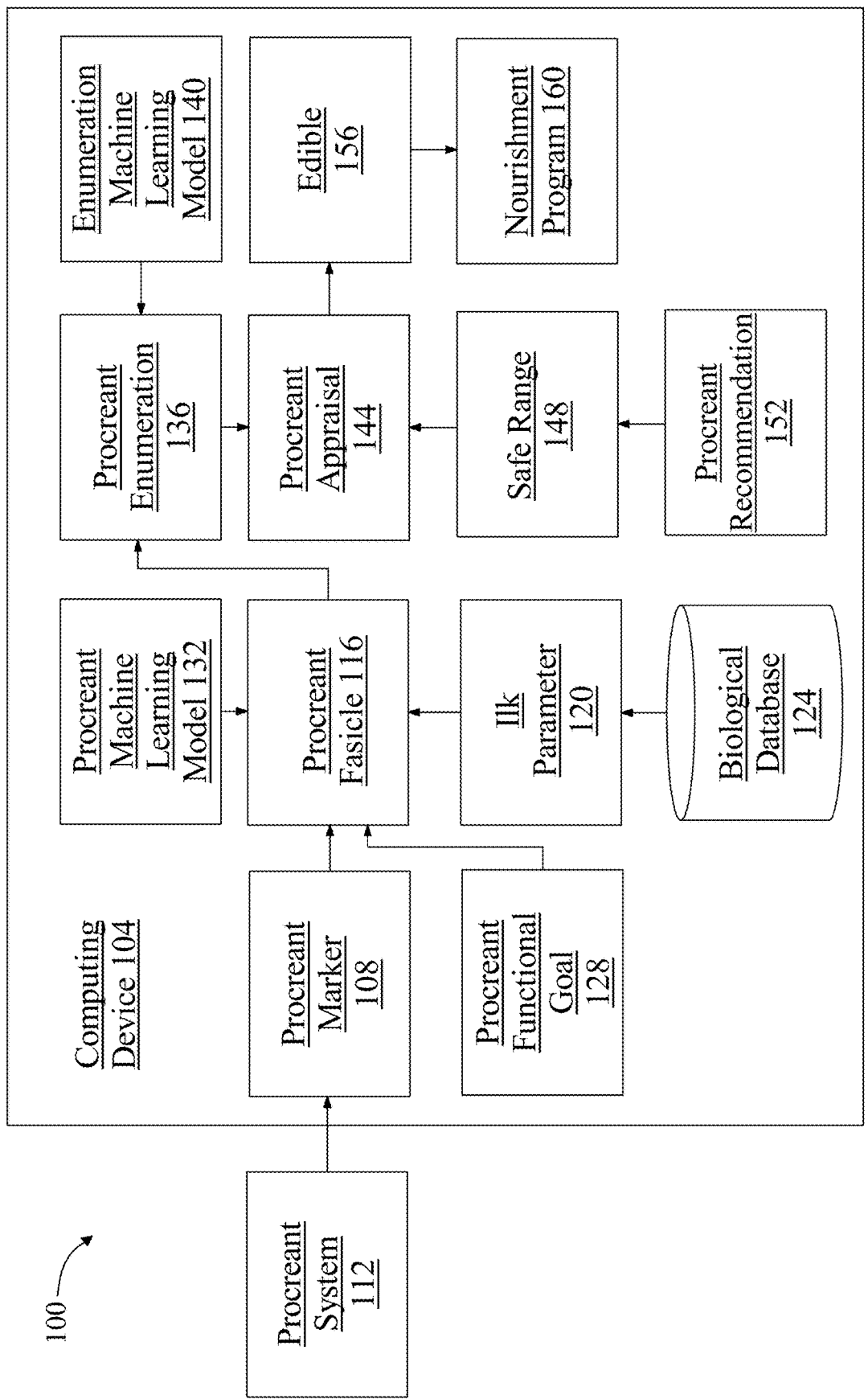
FIG. 1 is a block diagram illustrating an exemplary embodiment of a system for generating a procreant nourishment program.

Referring now to FIG. 1, an exemplary embodiment of a system 100 for generating a procreant nourishment program is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or as a function of a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 obtains at least a procreant marker 108. As used in this disclosure "procreant marker" is a marker that represents a health status of a user's procreant system. Procreant marker 108 may include a biological sample. As used in this disclosure "biological sample" is one or more biological specimens collected as a function of an individual. Biological sample may include, without limitation, blood, breath, sputum, urine, saliva, feces, semen, mucus, vaginal fluids, sebaceous oils, and other bodily fluids, as well as tissue. Procreant marker 108 may include tissue samples and/or cell samples from reproductive organs, wherein reproductive organs are described below. Procreant marker 108 may relate to one or more biomarkers. As used in this disclosure "biomarkers" are molecules, chemicals, components, and/or gases that at least identify the health status of a user's procreant system. As a non-limiting example biomarker may include, MLH1, MSH2, MSH6, PMS2, EPCAM, BRCA1, BRCA2, CHECK2, LH, FSH, progesterone, estrogen, androgen, prolactin, SHBG, testosterone, insulin, IGF1, IGF binding protein-1, PTEN genes, sterol regulatory binding protein-1, adiponectin, and the like thereof. As a non-limiting example procreant marker 108 may include a marker of androgen in a blood sample of an individual. As a further non-limiting example procreant marker 108 may include a hepatic cP450 in a bile sample of an individual. Procreant marker 108 is obtained as a function of a procreant system 112. As used in this disclosure "procreant system" is the reproductive system of an individual, wherein the reproductive system may include organs that contribute to the reproductive function of the human body. Organs of the reproductive system may include, without limitation, the ovary, fallopian tube, vagina, testes, uterus, penis, seminal vesicles, prostate, vas deferens, breasts, and the like thereof.

Still referring to FIG. 1, computing device 104 may obtain procreant marker 108 by receiving a procreant signal as a function of a sensor. As used in this disclosure "procreant signal" is datum that relates to and/or represents an element associated with the status of an individual's procreant system. As a non-limiting example a procreant signal may include an image of an ovary of an individual as a function of a magnetic resonance imaging medical device. As a further non-limiting example a procreant signal may include one or more lights, voltages, currents, sounds, chemicals, pressures, moistures, and the like thereof. As used in this disclosure "sensor" is a device that records, monitors, stores, measures, and/or transmits procreant signals. As a non-limiting example, a sensor may include an imaging sensor, such as optical cameras, infrared cameras, 3D cameras, multispectral cameras, hyperspectral cameras, polarized cameras, chemical sensors, motion sensors, ranging sensors, light radar component, such as lidar, detection or imaging using radio frequencies component, such as radar, terahertz or millimeter wave imagers, seismic sensors, magnetic sensors, weight/mass sensors, ionizing radiation sensors, and/or acoustical sensors. As a further non-limiting example, a sensor may include one or more medical examination devices. As used in this disclosure "medical examination devices" are devices that detect and/or monitor an individual's procreant system, such as semi-auto analyzers, photo colorimeters, cell photo colorimeters, hemoglobin meters, mass spectrometers, chromatographic instruments, and the like thereof.

Still referring to FIG. 1, computing device 104 identifies a procreant fascicle 116 as a function of procreant marker 108. As used in this disclosure "procreant fascicle" is a profile of a user's procreant status consisting of a group of procreant markers. Procreant fascicle may 116 may identify a profile as a function of sex, gender, reproductive organs, location of procreant marker origination, location of procreant marker termination, and the like thereof. As a non-limiting example procreant fascicle may identify a profile consisting of a group of procreant markers such as follicle stimulating hormone, estrogen, luteinizing hormone, progesterone, testosterone, dehydroepiandrosterone, cortisol, sex hormone binding globulin, triiodothyronine, thyroxine, thyroid stimulating hormone, and thyroid peroxidase antibodies relating to fertility of an individual. As a further non-limiting example, procreant fascicle 116 may identify a profile consisting of a group of procreant markers such as IL-1, IL-6, and CPK-MM relating to epididymitis of an individual. Computing device 104 identifies procreant fascicle 116 by receiving an ilk parameter 120. As used in this disclosure "ilk parameter" is a parameter associated with one or more biological classification elements. As a non-limiting example, ilk parameters may include sex, gender, culture, age, ethnicity, and the like thereof. Ilk parameter 120 is received as a function of a biological database 124, wherein a biological database identifies one or more ilk parameters associated with procreant system 112, as described below in detail, in reference to FIG. 5.

Still referring to FIG. 1, computing device 104 may classify a user datum to an ilk parameter. As used in this disclosure "user datum" is one or more biological classification elements associated with a user. For example, user datum may include a user's age, weight, height, reproductive goals, sex, gender, location, career, and the like thereof. Computing device 104 may classify user datum to at least identify one or more procreant commonalities among users. As used in this disclosure "procreant commonalities" are similarities that exist among two or more users that have similar ilk parameters. As a non-limiting example, procreant commonalities may identify that a midwestern suburban trans-male over the age of 50 may share similar reproductive goals of reducing fertility. As a further non-limiting example, procreant commonalities may identify that northeastern rural cis-females in the age range of 20-30 may share similar menstruation complications.

Still referring to FIG. 1, computing device 104 identifies procreant fascicle 116 by retrieving at least a procreant functional goal 128. As used in this disclosure "procreant functional goal" is a user desire, wish, want, and/or urge to alter and/or address a user concern. For example, and without limitation procreant functional goal 128 may include enhancing a user fertility. As a further non-limiting example procreant functional goal 128 may include reducing fertility and avoiding procreation. As a further non-limiting example procreant functional goal 128 may include a desire to enhance sexual performance and/or address erectile dysfunction concerns. As a further non-limiting example procreant functional goal 128 may include addressing irregular and/or painful menstruation cycles. Additionally and/or alternatively procreant functional goal may include a desire and/or wish to mitigate and/or diminish the effects of perimenopause and/or menopause. As a further non-limiting example procreant functional goal 128 may include a desire to adjust and/or alter hormone concentrations in an individual's body. Computing device 104 identifies procreant fascicle 116 as a function of ilk parameter 120, procreant functional goal 128, and procreant marker 108 using a procreant machine-learning model 132. As used in this disclosure "procreant machine-learning model" is a machine-learning model to produce a procreant fascicle output given ilk parameters, procreant functional goals, and procreant markers as inputs; this is in contrast to a non-machine learning software program where the commands to be executed are determined in advance by a user and written in a programming language. Procreant machine-learning model 132 may include one or more procreant machine-learning processes such as supervised, unsupervised, or reinforcement machine-learning processes that computing device 104 and/or a remote device may or may not use in the determination of procreant fascicle 116. As used in this disclosure "remote device" is an external device to computing device 104. A procreant machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train procreant machine-learning process as a function of a procreant training set. As used in this disclosure "procreant training set" is a training set that correlates an ilk parameter, procreant functional goal, and/or procreant marker to a procreant fascicle. For example, and without limitation, a procreant functional goal of hormone replacement, an ilk parameter of gender misassignment, and a procreant marker of an estrogen concentration of 124 pg/mL may relate to a procreant fascicle of trans-gender. As a further non-limiting example, a procreant functional goal of reduced scrotal pain, an ilk parameter of a male sex, and a procreant marker of IL-6 may relate to a procreant fascicle of inflammation of the epididymis. The procreant training set may be received as a function of user-entered valuations of ilk parameters, procreant functional goals, procreant markers, and/or procreant fascicles. Computing device 104 may receive procreant training by receiving correlations of ilk parameters, procreant functional goals, and or procreant markers that were previously received and/or determined during a previous iteration of determining procreant fascicles. The procreant training set may be received by one or more remote devices that at least correlate an ilk parameter, procreant functional goal, and/or procreant marker to a procreant fascicle, wherein a remote device is an external device to computing device 104, as described above. The procreant training set may be received by one or more user-entered correlations of an ilk parameter, procreant functional goal, and/or procreant marker to a procreant fascicle. Additionally or alternatively, a user may include an informed advisor, wherein an informed advisor may include, without limitation, urologists, reproductive endocrinologists, andrologists, reproductive immunologists, obstetrician-gynecologist, family physicians, family physicians, and the like thereof.

Still referring to FIG. 1, computing device 104 may receive procreant machine-learning model from a remote device that utilizes one or more procreant machine learning processes, wherein a remote device is described above in detail. For example, and without limitation, a remote device may include a computing device, external device, processor, and the like thereof. Remote device may perform the procreant machine-learning process using the procreant training set to generate procreant fascicle 128 and transmit the output to computing device 104. Remote device may transmit a signal, bit, datum, or parameter to computing device 104 that at least relates to procreant fascicle 128. Additionally or alternatively, the remote device may provide an updated machine-learning model. For example, and without limitation, an updated machine-learning model may be comprised of a firmware update, a software update, a procreant machine-learning process correction, and the like thereof. As a non-limiting example a software update may incorporate a new ilk parameter that relates to a modified procreant functional goal. Additionally or alternatively, the updated machine learning model may be transmitted to the remote device, wherein the remote device may replace the procreant machine-learning model with the updated machine-learning model and determine the procreant fascicle as a function of the ilk parameter using the updated machine-learning model. The updated machine-learning model may be transmitted by the remote device and received by computing device 104 as a software update, firmware update, or corrected procreant machine-learning model. For example, and without limitation a procreant machine-learning model may utilize a random forest machine-learning process, wherein the updated machine-learning model may incorporate a gradient boosting machine-learning process. Updated machine learning model may additionally or alternatively include any machine-learning model used as an updated machine learning model as described in U.S. Nonprovisional application Ser. No. 17/106,658, filed on Nov. 30, 2020, and entitled "A SYSTEM AND METHOD FOR GENERATING A DYNAMIC WEIGHTED COMBINATION," the entirety of which is incorporated herein by reference.

Still referring to FIG. 1, computing device 104 may identify procreant fascicle 116 by receiving a synergistic parameter as a function of procreant marker 108, wherein a synergistic parameter is a parameter that identifies one or more additional biomarkers that contribute to the same function in the human body described below in detail, in reference to FIG. 3. Computing device 104 may generate a procreant cluster as a function of synergistic parameter. As used in this disclosure "procreant cluster" is a cluster of is one or more procreant functions. As a non-limiting example procreant cluster may include one or more procreant functions associated with the production of egg cells. As a further non-limiting example procreant cluster may include one or more procreant functions associated with the production of spermatozoa. As a further non-limiting example procreant cluster may include one or more procreant functions associated with pregnancy and/or childbirth. As a further non-limiting example, procreant cluster may include one or more reproductive functions associated with puberty and/or maturation. Computing device 104 may identify procreant fascicle 116 as a function of procreant cluster.

Still referring to FIG. 1, procreant machine-learning model 132 may include a k-means clustering algorithm. A "k-means clustering algorithm" as used in this disclosure, includes cluster analysis that partitions n observations or unclassified cluster data entries into k clusters in which each observation or unclassified cluster data entry belongs to the cluster with the nearest mean, using, for instance behavioral training set as described above. "Cluster analysis" as used in this disclosure, includes grouping a set of observations or data entries in way that observations or data entries in the same group or cluster are more similar to each other than to those in other groups or clusters. Cluster analysis may be performed by various cluster models that include connectivity models such as hierarchical clustering, centroid models such as k-means, distribution models such as multivariate normal distribution, density models such as density-based spatial clustering of applications with nose (DBSCAN) and ordering points to identify the clustering structure (OPTICS), subspace models such as biclustering, group models, graph-based models such as a clique, signed graph models, neural models, and the like. Cluster analysis may include hard clustering whereby each observation or unclassified cluster data entry belongs to a cluster or not. Cluster analysis may include soft clustering or fuzzy clustering whereby each observation or unclassified cluster data entry belongs to each cluster to a certain degree such as for example a likelihood of belonging to a cluster; for instance, and without limitation, a fuzzy clustering algorithm may be used to identify clustering of gene combinations with multiple disease states, and vice versa. Cluster analysis may include strict partitioning clustering whereby each observation or unclassified cluster data entry belongs to exactly one cluster. Cluster analysis may include strict partitioning clustering with outliers whereby observations or unclassified cluster data entries may belong to no cluster and may be considered outliers. Cluster analysis may include overlapping clustering whereby observations or unclassified cluster data entries may belong to more than one cluster. Cluster analysis may include hierarchical clustering whereby observations or unclassified cluster data entries that belong to a child cluster also belong to a parent cluster.

With continued reference to FIG. 1, computing device may generate a k-means clustering algorithm receiving unclassified physiological state data and outputs a definite number of classified data entry clusters wherein the data entry clusters each contain cluster data entries. K-means algorithm may select a specific number of groups or clusters to output, identified by a variable "k." Generating a k-means clustering algorithm includes assigning inputs containing unclassified data to a "k-group" or "k-cluster" based on feature similarity. Centroids of k-groups or k-clusters may be utilized to generate classified data entry cluster. K-means clustering algorithm may select and/or be provided "k" variable by calculating k-means clustering algorithm for a range of k values and comparing results. K-means clustering algorithm may compare results across different values of k as the mean distance between cluster data entries and cluster centroid. K-means clustering algorithm may calculate mean distance to a centroid as a function of k value, and the location of where the rate of decrease starts to sharply shift, this may be utilized to select a k value. Centroids of k-groups or k-cluster include a collection of feature values which are utilized to classify data entry clusters containing cluster data entries. K-means clustering algorithm may act to identify clusters of closely related physiological data, which may be provided with user cohort labels; this may, for instance, generate an initial set of user cohort labels from an initial set of user physiological data of a large number of users, and may also, upon subsequent iterations, identify new clusters to be provided new user cohort labels, to which additional user physiological data may be classified, or to which previously used user physiological data may be reclassified.

With continued reference to FIG. 1, generating a k-means clustering algorithm may include generating initial estimates for k centroids which may be randomly generated or randomly selected from unclassified data input. K centroids may be utilized to define one or more clusters. K-means clustering algorithm may assign unclassified data to one or more k-centroids based on the squared Euclidean distance by first performing a data assigned step of unclassified data. K-means clustering algorithm may assign unclassified data to its nearest centroid based on the collection of centroids ci of centroids in set C. Unclassified data may be assigned to a cluster based on $\text{argmin}_{ci \in C} \text{dist}(ci, x)^2$, where argmin includes argument of the minimum, ci includes a collection of centroids in a set C, and dist includes standard Euclidean distance. K-means clustering module may then recompute centroids by taking mean of all cluster data entries assigned to a centroid's cluster. This may be calculated based on $ci = 1/|Si| \Sigma xi \in Si^{xi}$ K-means clustering algorithm may continue to repeat these calculations until a stopping criterion has been satisfied such as when cluster data entries do not change clusters, the sum of the distances have been minimized, and/or some maximum number of iterations has been reached.

Still referring to FIG. 1, k-means clustering algorithm may be configured to calculate a degree of similarity index value. A "degree of similarity index value" as used in this disclosure, includes a distance measurement indicating a measurement between each data entry cluster generated by k-means clustering algorithm and a selected physiological data set. Degree of similarity index value may indicate how close a particular combination of genes, negative behaviors and/or negative behavioral propensities is to being classified by k-means algorithm to a particular cluster. K-means clustering algorithm may evaluate the distances of the combination of genes, negative behaviors and/or negative behavioral propensities to the k-number of clusters output by k-means clustering algorithm. Short distances between a set of physiological data and a cluster may indicate a higher degree of similarity between the set of physiological data and a particular cluster. Longer distances between a set of physiological behavior and a cluster may indicate a lower degree of similarity between a physiological data set and a particular cluster.

With continued reference to FIG. 1, k-means clustering algorithm selects a classified data entry cluster as a function of the degree of similarity index value. In an embodiment, k-means clustering algorithm may select a classified data entry cluster with the smallest degree of similarity index value indicating a high degree of similarity between a physiological data set and the data entry cluster. Alternatively or additionally k-means clustering algorithm may select a plurality of clusters having low degree of similarity index values to physiological data sets, indicative of greater degrees of similarity. Degree of similarity index values may be compared to a threshold number indicating a minimal degree of relatedness suitable for inclusion of a set of physiological data in a cluster, where degree of similarity indices a-n falling under the threshold number may be included as indicative of high degrees of relatedness. The above-described illustration of feature learning using k-means clustering is included for illustrative purposes only, and should not be construed as limiting potential implementation of feature learning algorithms; persons skilled in the art, upon reviewing the entirety of this disclosure, will be aware of various additional or alternative feature learning and/or clustering approaches that may be used consistently with this disclosure, including without limitation clustering algorithms based on particle swarm optimization (PSO), ant colony optimization (ACO), neural networks, deep learning networks, and the like.

Still referring to FIG. 1, computing device 104 produces a procreant enumeration 136. As used in this this disclosure "procreant enumeration" is a measurable value associated with a procreant impact. As a non-limiting example procreant enumeration 136 may be a value of 13 for a procreant impact of sterility. As a further non-limiting example procreant enumeration 136 may be a value of 25 for a procreant impact of severe abdominal cramps. Computing device 104 determines procreant enumeration 136 using an enumeration machine-learning model 140. As used in this disclosure "enumeration machine-learning model" is a machine-learning model to produce a procreant enumeration output given a procreant fascicle and procreant impacts as inputs; this is in contrast to a non-machine learning software program where the commands to be executed are determined in advance by a user and written in a programming language. Enumeration machine-learning model may include one or more enumeration machine-learning processes such as supervised, unsupervised, or reinforcement machine-learning processes that computing device 104 and/or a remote device may or may not use in the determination of procreant appraisal. An enumeration machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train enumeration machine-learning process as a function of an enumeration training set. As used in this disclosure "enumeration training set" is a training set that correlates at least a procreant fascicle to a procreant impact. As a non-limiting example a procreant fascicle of reduced fertility may relate to a procreant impact of 36. The enumeration training set may be received as a function of user-entered valuations of procreant fascicle, procreant impact, and/or procreant enumeration. Computing device 104 may receive enumeration training by receiving correlations of a procreant fascicles and/or procreant impacts that were previously received and/or determined during a previous iteration of determining procreant enumeration. The enumeration training set may be received by one or more remote devices that at least correlate procreant fascicles and/or procreant impacts to procreant enumeration, wherein a remote device is an external device to computing device 104, as described above. The enumeration training set may be received by one or more user-entered correlations of a procreant fascicle and/or procreant impact to procreant enumeration. Additionally or alternatively, a user may include an informed advisor, wherein an informed advisor may include, without limitation, urologists, reproductive endocrinologists, andrologists, reproductive immunologists, obstetrician-gynecologist, family physicians, and the like thereof.

Still referring to FIG. 1, computing device 104 may receive enumeration machine-learning model 152 from a remote device that utilizes one or more enumeration machine learning processes, wherein a remote device is described above in detail. For example, and without limitation, a remote device may include a computing device, external device, processor, and the like thereof. Remote device may perform the enumeration machine-learning process using the enumeration training set to generate procreant enumeration and transmit the output to computing device 104. Remote device may transmit a signal, bit, datum, or parameter to computing device 104 that at least relates to a procreant enumerations. Additionally or alternatively, the remote device may provide an updated machine-learning model. For example, and without limitation, an updated machine-learning model may be comprised of a firmware update, a software update, an enumeration machine-learning process correction, and the like thereof. As a non-limiting example a software update may incorporate a new procreant fascicle that relates to a modified procreant impact. Additionally or alternatively, the updated machine learning model may be transmitted to the remote device, wherein the remote device may replace the enumeration machine-learning model with the updated machine-learning model and determine the procreant enumeration as a function of the procreant impact using the updated machine-learning model. The updated machine-learning model may be transmitted by the remote device and received by computing device 104 as a software update, firmware update, or corrected enumeration machine-learning model. For example, and without limitation procreant machine-learning model may utilize a logistic classification machine-learning process, wherein the updated machine-learning model may incorporate linear discriminant analysis machine-learning process.

Still referring to FIG. 1, computing device 104 may produce procreant enumeration 136 by identifying a procreant disorder. As used in this disclosure "procreant disorder" is an ailment and/or collection of ailments that impact an individual's reproductive system. As a non-limiting example, procreant disorder may include prostate cancer, testicular cancer, prostatitis, erectile dysfunction, male infertility, testosterone deficiency, epididymitis varicocele, Lynch syndrome, endometriosis, uterine fibroids, dysmenorrhea, cervical cancer, familial breast cancer, pelvic inflammatory disease, and the like thereof. Procreant disorder may be identified as a function of one or more disorder machine-learning models. As used in this disclosure "disorder machine-learning model" is a machine-learning model to produce a procreant disorder output given procreant fascicles as inputs; this is in contrast to a non-machine learning software program where the commands to be executed are determined in advance by a user and written in a programming language. Disorder machine-learning model may include one or more disorder machine-learning processes such as supervised, unsupervised, or reinforcement machine-learning processes that computing device 104 and/or a remote device may or may not use in the determination of procreant disorder. A disorder machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train disorder machine-learning process as a function of a disorder training set. As used in this disclosure "disorder training set" is a training set that correlates at least a procreant system effect and procreant fascicle 116 to a procreant disorder. As used in this disclosure "procreant system effect" is an impact and/or effect on the procreant system of an individual. As a non-limiting example a procreant fascicle of reduced testosterone may be established for a procreant system effect of infertility, wherein a procreant disorder of infertility may be determined. The disorder training set may be received as a function of user-entered valuations of procreant fascicle 116, procreant system effects, and/or procreant disorders. Computing device 104 may receive disorder training by receiving correlations of procreant fascicle 116 and/or procreant system effects that were previously received and/or determined during a previous iteration of determining procreant disorders. The disorder training set may be received by one or more remote devices that at least correlate procreant fascicle 116 and/or procreant system effect to a procreant disorder, wherein a remote device is an external device to computing device 104, as described above. The disorder training set may be received by one or more user-entered correlations of a procreant fascicle and procreant system effect to a procreant disorder. Additionally or alternatively, a user may include an informed advisor, wherein an informed advisor may include, without limitation, urologists, reproductive endocrinologists, andrologists, reproductive immunologists, obstetrician-gynecologist, family physicians, and the like thereof.

Still referring to FIG. 1, computing device 104 may receive disorder machine-learning model from a remote device that utilizes one or more disorder machine learning processes, wherein a remote device is described above in detail. For example, and without limitation, a remote device may include a computing device, external device, processor, and the like thereof. Remote device may perform the disorder machine-learning process using the disorder training set to generate procreant disorder and transmit the output to computing device 104. Remote device may transmit a signal, bit, datum, or parameter to computing device 104 that at least relates to procreant disorders. Additionally or alternatively, the remote device may provide an updated machine-learning model. For example, and without limitation, an updated machine-learning model may be comprised of a firmware update, a software update, a disorder machine-learning process correction, and the like thereof. As a non-limiting example a software update may incorporate a new procreant fascicle that relates to a modified procreant system effect. Additionally or alternatively, the updated machine learning model may be transmitted to the remote device, wherein the remote device may replace the disorder machine-learning model with the updated machine-learning model and determine the procreant disorder as a function of the procreant fascicle using the updated machine-learning model. The updated machine-learning model may be transmitted by the remote device and received by computing device 104 as a software update, firmware update, or corrected dysfunction machine-learning model. For example, and without limitation procreant machine-learning model may utilize a neural net machine-learning process, wherein the updated machine-learning model may incorporate hierarchical clustering machine-learning process.

Still referring to FIG. 1, computing device 104 determines a procreant appraisal 144 as a function of procreant enumeration 136. As used in this disclosure "procreant appraisal" is a quantitative value associated with the severity of procreant enumeration. Computing device 104 determines procreant appraisal 144 by receiving a safe range 148.

As used in this disclosure "safe range" is a reference range and/or reference interval for a normal physiologic measurement of a procreant marker. As a non-limiting example procreant fascicle 116 may identify a serum endocannabinoid concentration of 5.2 nM, wherein a safe range of serum endocannabinoid concentrations for fertility may be 10-600 nM. As a further non-limiting example, procreant fascicle 116 may determine a HER2/neu concentration of 65.38 ng/mL, wherein a wherein a safe range of HER2/neu may be 12.2-25.6 ng/mL. Safe range 148 is received as a function of a procreant recommendation 152. As used in this disclosure "procreant recommendation" is a medical guideline for the measurement of procreant system health. As a non-limiting example procreant recommendation 152 may be identified by one or more organizations that relate to, represent, and/or study procreant functions in humans, such as The American Society for Reproductive Medicine, Reproductive Medicine Associates, Society for Assisted Reproductive Technology, and the like thereof. As a further non-limiting example, procreant recommendation 152 may determine safe range 148 as a function of one or more medical research journals, such as Reproductive Sciences, Reproductive Biomedicine Online, Reproductions, Biology of Reproduction, The Lancet, New England Journal of Medicine, Science, Journal of the American Medical Association, and the like thereof.

Still referring to FIG. 1, Computing device 104 may determine procreant appraisal 136 as a function of generating a degree of variance. As used in this disclosure "degree of variance" is a quantitative value comprising the magnitude of divergence of procreant enumeration 148 and safe range 140. As a non-limiting example, a degree of variance may be 12 for a procreant enumeration of 0.22 µg/mL of progesterone, wherein the safe range 0.08-0.12 µg/mL of progesterone. Degree of variance may include a transgression parameter. As used in this disclosure "transgression parameter" is a parameter that identifies one or more degrees of variance that exceed a variance limit. As a non-limiting example, transgression parameter may determine that a degree of variance should not exceed 10 for the biomarker inhibin. As a further non-limiting, transgression parameter may determine that a degree of variance should not exceed 2 for a vascular endothelial growth factor.

Still referring to FIG. 1, computing device 104 ascertains at least an edible 156 as a function of procreant appraisal 144. As used in this disclosure an "edible" is a source of nourishment that may be consumed by a user such that the user may absorb the nutrients from the source. For example and without limitation, an edible may include legumes, plants, fungi, nuts, seeds, breads, dairy, eggs, meat, cereals, rice, seafood, desserts, dried foods, dumplings, pies, noodles, salads, stews, soups, sauces, sandwiches, and the like thereof. Computing device 104 may ascertain edible 156 as a function of obtaining a nourishment composition. As used in this disclosure "nourishment composition" is a list and/or compilation of all of the nutrients contained in an edible. As a non-limiting example nourishment composition may include one or more quantities and/or amounts of total fat, including saturated fat and/or trans-fat, cholesterol, sodium, total carbohydrates, including dietary fiber and/or total sugars, protein, vitamin A, vitamin C, thiamin, riboflavin, niacin, pantothenic acid, vitamin b6, folate, biotin, vitamin B12, vitamin D, vitamin E, vitamin K, calcium, iron, phosphorous, iodine, magnesium, zinc, selenium, copper, manganese, chromium, molybdenum, chloride, and the like thereof. Nourishment composition may be obtained as a function of an edible directory, wherein an edible directory is a database of edibles that may be identified as a function of one or more procreant appraisals, as described in detail below, in reference to FIG. 4.

Still referring to FIG. 1, computing device 104 may ascertain edible 156 as a function of nourishment composition, procreant appraisal 144, and an edible machine-learning model. As used in this disclosure "edible machine-learning model" is a machine-learning model to produce an edible output given nourishment compositions and procreant appraisals as inputs; this is in contrast to a non-machine learning software program where the commands to be executed are determined in advance by a user and written in a programming language. Edible machine-learning model may include one or more edible machine-learning processes such as supervised, unsupervised, or reinforcement machine-learning processes that computing device 104 and/or a remote device may or may not use in ascertaining edible 156. An edible machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train edible machine-learning process as a function of an edible training set. As used in this disclosure a "edible training set" is a training set that correlates at least nourishment composition and procreant appraisal to an edible. For example, and without limitation, nourishment composition of 600 ng/mL of estrogen and a procreant appraisal of infertility may relate to an edible of edamame. The edible training set may be received as a function of user-entered valuations of nourishment compositions, procreant appraisals, and/or edibles. Computing device 104 may receive edible training by receiving correlations of nourishment compositions and/or procreant appraisals that were previously received and/or determined during a previous iteration of ascertaining edibles. The edible training set may be received by one or more remote devices that at least correlate a nourishment composition and procreant appraisal to an edible, wherein a remote device is an external device to computing device 104, as described above. The edible training set may be received by one or more user-entered correlations of a nourishment composition and procreant appraisal to an edible. Additionally or alternatively, a user may include an informed advisor, wherein an informed advisor may include, without limitation, urologists, reproductive endocrinologists, andrologists, reproductive immunologists, obstetrician-gynecologist, family physicians, and the like thereof.

Still referring to FIG. 1, edible machine-learning model may ascertain edible 156 as a function of one or more classifiers. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate a classifier using a classification algorithm, defined as a processes whereby a computing device 104 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, computing device 104 may be configured to generate a classifier using a Naïve Bayes classification algorithm. Naïve Bayes classification algorithm generates classifiers by assigning class labels to problem instances, represented as vectors of element values. Class labels are drawn as a function of a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A)\div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least one value. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\Sigma_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, computing device 104 may receive edible machine-learning model from a remote device that utilizes one or more edible machine learning processes, wherein a remote device is described above in detail. For example, and without limitation, a remote device may include a computing device, external device, processor, and the like thereof. Remote device may perform the edible machine-learning process using the edible training set to ascertain edible 156 and transmit the output to computing device 104. Remote device may transmit a signal, bit, datum, or parameter to computing device 104 that at least relates to edible 156. Additionally or alternatively, the remote device may provide an updated machine-learning model. For example, and without limitation, an updated machine-learning model may be comprised of a firmware update, a software update, an edible machine-learning process correction, and the like thereof. As a non-limiting example a software update may incorporate a new nourishment composition that relates to a modified procreant appraisal. Additionally or alternatively, the updated machine learning model may be transmitted to the remote device, wherein the remote device may replace the edible machine-learning model with the updated machine-learning model and ascertain the edible as a function of the procreant appraisal using the updated machine-learning model. The updated machine-learning model may be transmitted by the remote device and received by computing device 104 as a software update, firmware update, or corrected edible machine-learning model. For example, and without limitation an edible machine-learning model may utilize a Naïve Bayes machine-learning process, wherein the updated machine-learning model may incorporate a logistic regression machine-learning process. Updated machine learning model may additionally or alternatively include any machine-learning model used as an updated machine learning model as described in U.S. Nonprovisional application Ser. No. 17/106,658.

Still referring to FIG. 1, computing device 104 may ascertain edible 156 as a function of a likelihood parameter. As used in this disclosure "likelihood parameter" is a parameter that identities the probability of a user to consume an edible. As a non-limiting example likelihood parameter may identify a high probability that a user will consume an edible of chicken. As a further non-limiting example likelihood parameter may identify a low probability that a user will consume an edible of Brussel sprouts. Likelihood parameter may be determined as a function of a user taste profile. As used in this disclosure "user taste profile" is a profile of a user that identifies one or more desires, preferences, wishes, and/or wants that a user has. As a non-limiting example a user taste profile may include a user's preference for beef flavor and/or soft textured edibles. Likelihood parameter may be determined as a function of an edible profile. As used in this disclosure "edible profile" is taste of an edible is the sensation of flavor perceived in the mouth and throat on contact with the edible. Edible profile may include one or more flavor variables. As used in this disclosure "flavor variable" is a variable associated with the distinctive taste of an edible, wherein a distinctive may include, without limitation sweet, bitter, sour, salty, umami, cool, and/or hot. Edible profile may be determined as a function of receiving flavor variable as a function of a flavor directory. As used in this disclosure "flavor directory" is a database of flavors for an edible. As a non-limiting example flavor directory may include a list and/or collection of edibles that all contain umami flavor variables. As a further non-limiting example flavor directory may include a list and/or collection of edibles that all contain sour flavor variables. Likelihood parameter may alternatively or additionally include any user taste profile and/or edible profile used as a likelihood parameter as described in U.S. Nonprovisional application Ser. No. 17/032,080, filed on Sep. 25, 2020, and entitled "METHODS, SYSTEMS, AND DEVICES FOR GENERATING A REFRESHMENT INSTRUCTION SET BASED ON INDIVIDUAL PREFERENCES," the entirety of which is incorporated herein by reference.

Still referring to FIG. 1, computing device 104 generates a nourishment program 160 of a plurality of nourishment programs as a function of edible 156. As used in this disclosure "nourishment program" is a program consisting of one or more edibles that are to be consumed over a given time period, wherein a time period is a temporal measurement such as seconds, minutes, hours, days, weeks, months, years, and the like thereof. As a non-limiting example nourishment program 160 may consist of recommending ice cream for 2 days. As a further non-limiting example nourishment program 160 may recommend tofu for a first day, quinoa for a second day, and broccoli for a third day. Nourishment program 160 may include one or more diet programs such as paleo, keto, vegan, vegetarian, and the like thereof. Computing device 104 generates nourishment program as a function of a procreant outcome. As used in this disclosure "procreant outcome" is an outcome that an edible may generate according to a predicted and/or purposeful plan. As a non-limiting example, procreant outcome may include a treatment outcome. As used in this disclosure "treatment outcome" is an intended outcome that is designed to at least reverse and/or eliminate procreant appraisal 144 associated with procreant fascicle 116 and/or procreant disorder. As a non-limiting example, a treatment outcome may include reversing the effects of the procreant disorder of endometriosis. As a further non-limiting example, a treatment outcome includes reversing the procreant disorder of dysmenorrhea. Procreant outcome may include a prevention outcome. As used in this disclosure "prevention outcome" is an intended outcome that is designed to at least prevent and/or avert procreant appraisal 144 associated with procreant fascicle 116 and/or procreant disorder. As a non-limiting example, a prevention outcome may include preventing the development of the procreant disorder of infertility.

Still referring to FIG. 1, computing device 104 may generate nourishment program 160 function of edible 156 and procreant outcome using a nourishment machine-learning model. As used in this disclosure "nourishment machine-learning model" is a machine-learning model to produce a nourishment program output given edibles and/or procreant outcomes as inputs; this is in contrast to a non-machine learning software program where the commands to be executed are determined in advance by a user and written in a programming language. Nourishment machine-learning model may include one or more nourishment machine-learning processes such as supervised, unsupervised, or reinforcement machine-learning processes that computing device 104 and/or a remote device may or may not use in the determination of nourishment program 160. Nourishment machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train nourishment machine-learning process as a function of a nourishment training set. As used in this disclosure a "nourishment training set" is a training set that correlates a procreant outcome to an edible. The nourishment training set may be received as a function of user-entered edibles, procreant outcomes, and/or nourishment programs. Computing device 104 may receive nourishment training by receiving correlations of procreant outcomes and/or edibles that were previously received and/or determined during a previous iteration of determining nourishment programs. The nourishment training set may be received by one or more remote devices that at least correlate a procreant outcome and/or edible to a nourishment program, wherein a remote device is an external device to computing device 104, as described above. The nourishment training set may be received by one or more user-entered correlations of a procreant outcome and edible to a nourishment program. Additionally or alternatively, a user may include an informed advisor, wherein an informed advisor may include, without limitation, urologists, reproductive endocrinologists, andrologists, reproductive immunologists, obstetrician-gynecologist, family physicians, and the like thereof.

Still referring to FIG. 1, computing device 104 may receive nourishment machine-learning model 156 from a remote device that utilizes one or more nourishment machine learning processes, wherein a remote device is described above in detail. For example, and without limitation, a remote device may include a computing device, external device, processor, and the like thereof. Remote device may perform the nourishment machine-learning process using the nourishment training set to generate nourishment program 160 and transmit the output to computing device 104. Remote device may transmit a signal, bit, datum, or parameter to computing device 104 that at least relates to nourishment program 160. Additionally or alternatively, the remote device may provide an updated machine-learning model. For example, and without limitation, an updated machine-learning model may be comprised of a firmware update, a software update, a nourishment machine-learning process correction, and the like thereof. As a non-limiting example a software update may incorporate a new procreant outcome that relates to a modified edible. Additionally or alternatively, the updated machine learning model may be transmitted to the remote device, wherein the remote device may replace the nourishment machine-learning model with the updated machine-learning model and determine the nourishment program as a function of the procreant outcome using the updated machine-learning model. The updated machine-learning model may be transmitted by the remote device and received by computing device 104 as a software update, firmware update, or corrected nourishment machine-learning model. For example, and without limitation nourishment machine-learning model may utilize a decision tree machine-learning process, wherein the updated machine-learning model may incorporate linear regression machine-learning processes.

Figure 2:
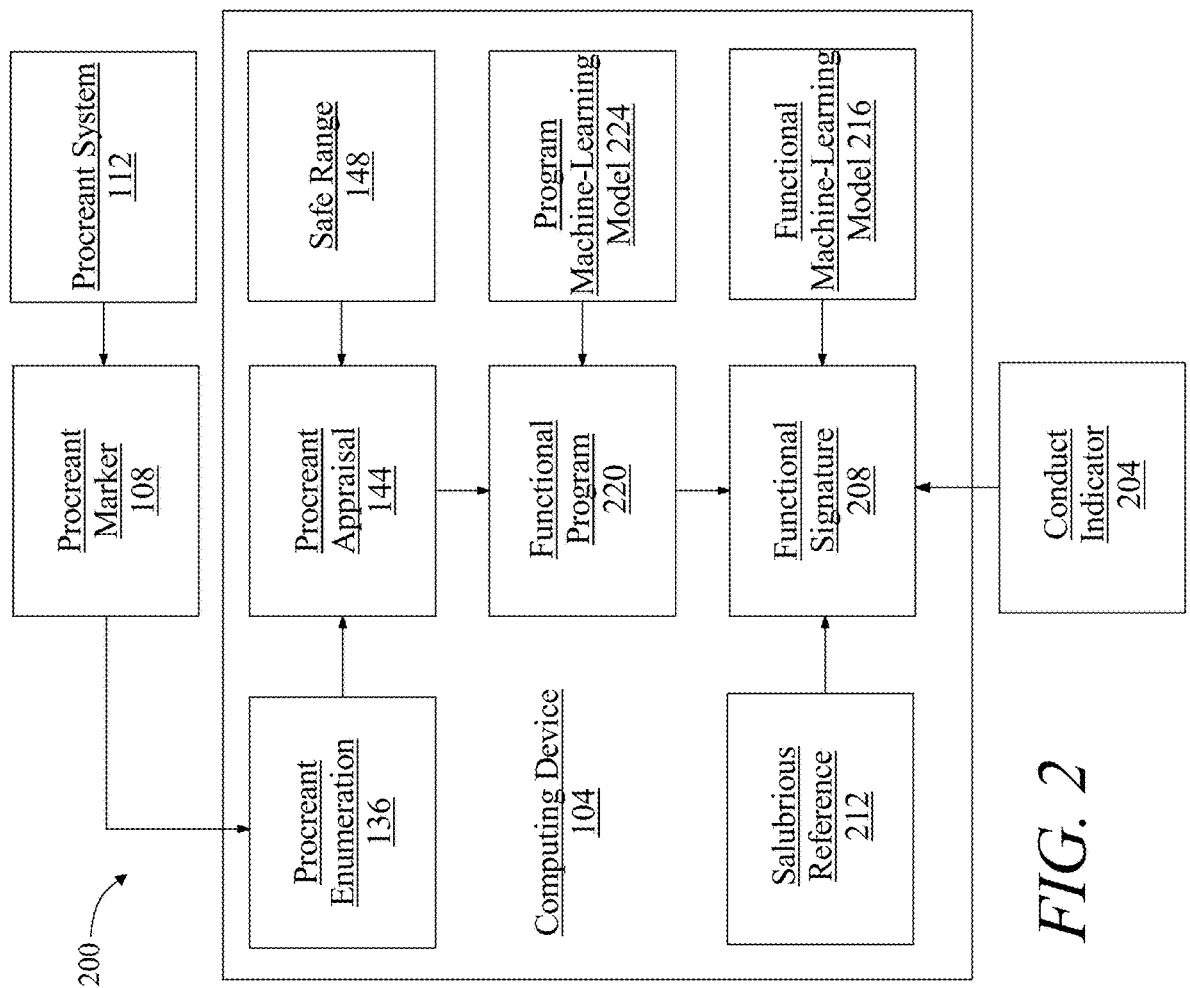
FIG. 2 is a block diagram illustrating an exemplary embodiment of a system for generating a procreant functional program.

Now referring to FIG. 2, an exemplary embodiment of a system 200 for generating procreant functional program is illustrated. System 200 includes computing device 104. Computing device 104 may include any computing device 104 as described above in detail, in reference to FIG. 1. For example and without limitation, computing device 104 may include a microcontroller, microprocessor, digital signal processor (DSP) and/or system on a chip (SoC) as described in this disclosure. Computing device 104 is configured to obtain a procreant marker 108. Procreant marker 108 includes any of the procreant marker 108 as described above in detail, in reference to FIG. 1. For example, and without procreant marker 108 may include a marker that represents a health status of a user's procreant system such as, but not limited to a biological sample, biomarkers, procreant signal, and the like thereof. Procreant marker 108 may be obtained as a function of a procreant system 112. Procreant system 112 may include any of the procreant system 112 as described above in detail, in reference to FIG. 1. For example, and without limitation, procreant system 112 may include any cells, tissues, and/or organs associated with reproduction and/or procreation such as, but not limited to the ovary, fallopian tube, vagina, testes, uterus, penis, seminal vesicles, prostate, vas deferens, breasts, and the like thereof.

Still referring to FIG. 2, computing device 104 determines a procreant appraisal 144 as a function of procreant marker 108. Procreant appraisal 144 may include any of the procreant appraisal as described above in detail, in reference to FIG. 1. Computing device 104 determines procreant appraisal 144 as a function of producing a procreant enumeration 136 as a function of procreant marker 108. Procreant enumeration 136 may include any of the procreant enumeration 136 as described above in detail, in reference to FIG. 1. For example, and without limitation, procreant enumeration 136 may be a value of 71 for reduced spermatozoa motility. In an embodiment, computing device 104 may produce procreant enumeration 136 as a function of identifying a procreant disorder. Procreant disorder may include any of the procreant disorder as described above in detail, in reference to FIG. 1. For example, and without limitation, procreant disorder may include infertility, prostate cancer, testicular cancer, endometriosis, uterine fibroids, dysmenorrhea, cervical cancer, familial breast cancer, pelvic inflammatory disease, and the like thereof. Computing device 104 determines procreant appraisal 144 as a function of procreant enumeration 136 and a safe range 148. Safe range 148 may include any of the safe range 148 as described above in detail, in reference to FIG. 1. For example, and without limitation, safe range 148 may identify that endocannabinoid concentrations for fertility should be 15-350 pg/mL.

Still referring to FIG. 2, computing device 104 receives a conduct indicator 204. As used in this disclosure a "conduct indicator" is an element of data denoting an individual's lifestyle choices. In an embodiment conduct indicator 204 may include one or more biological, psychological, social, and/or spiritual elements. For example, and without limitation, conduct indicator 204 may denote a biological element, wherein the biological indicator may denote that an individual has low cholesterol and/or exercises frequently. As a further non-limiting example, conduct indicator 204 may denote a psychological element, wherein the psychological element may denote that an individual is happy and/or content. As a further non-limiting example, conduct indicator 204 may denote a social element, wherein the social element may indicate that an individual has 36 friends. As a further non-limiting example, conduct indicator 204 may denote a spiritual element, wherein the spiritual element may indicate that an individual belongs to the Hinduism religion. As a further non-limiting example, spiritual element may denote one or more chakras and/or spiritual energies of an individual. In an embodiment conduct indicator 204 may denote one or more lifestyles groups such as, but not limited to, general lifestyles, income, profession, and/or occupation lifestyles, consumption-based lifestyles, social and/or political lifestyles, marketing lifestyles, military lifestyles, sexual lifestyles, spiritual lifestyles, religious lifestyles, musical lifestyles, recreational lifestyles, and the like thereof. For example, and without limitation, lifestyles may include activism, asceticism, modern primitivism, bohemianism, communal living, clothes free, groupie lifestyle, hippie, quirkyalone, rural lifestyle, simple living, traditional lifestyle, criminality, farming, jet set, piracy, poverty, prostitution, sarariman, workaholic, yuppie, social liberalism, social conservatism, polygamy, monogamy, ahimsa, Hinduism, Christianity, evangelicalism, Islam, Judaism, missionary, Zen, yoga, Thelema, surfer, athleticism, hunter, artist, golf, recreational drug use, and the like thereof. Additionally or alternatively conduct indicator 204 may include one or more markers associated with an individual's behavior such as, but not limited to, markers identified as procreant marker 108. For example, and without limitation markers may include but are not limited to biological samples, biomarkers, procreant signals, and the like thereof as defined above, in reference to FIG. 1.

Still referring to FIG. 2, conduct indicator 204 may include a dimensional element. As used in this disclosure a "dimensional element" is an element of datum denoting a relative measure of wellness of an individual. For example, and without limitation dimensional element may denote one or more dimensions associated with healthy living. In an embodiment dimensional element may include an occupational dimension. As used in this disclosure an "occupational dimension" is a dimension of wellness representing personal satisfaction and enrichment in an individual's life through work and/or occupation. For example, and without limitation, occupational dimension may denote that an individual's job is rewarding due to the contribution of personal values, interests, and/or beliefs that are shared among the job and the individual. In an embodiment dimensional element may include a physical dimension. As used in this disclosure a "physical dimension" is a dimension of wellness representing physical activity and/or nutrition. For example, and without limitation, physical dimension may include a dimension associated with eating whole grain foods and/or lean protein foods diet and/or nutrition, while concurrently discouraging the use of recreational drugs. As a further non-limiting example, physical dimension may include a dimension associated with regular exercise and/or enhanced physical strength. In an embodiment dimensional element may include a social dimension. As used in this disclosure a "social dimension" is a dimension of wellness representing an individual's contributions towards the environment and/or community. For example, and without limitation, social dimension may include a dimension associated with an individual's contributions towards the common welfare of the community and/or living in harmony with other.

In an embodiment and still referring to FIG. 2, dimensional element may include an intellectual dimension. As used in this disclosure a "intellectual dimension" is a dimension of wellness representing an individual's creative and/or mental activities. For example, and without limitation, intellectual dimension may include a dimension associated with an individual's abilities to identify potential problems and choose appropriate courses of action based on available information than to wait, worry, and contend with major concerns later. In an embodiment dimensional element may include a spiritual dimension. As used in this disclosure a "spiritual dimension" is a dimension of wellness representing an individual's search for meaning and/or purpose of existence. For example, and without limitation, spiritual dimension may include a dimension associated with an individual's understanding of the meaning for existence and/or the tolerance of other's meaning for existence. In an embodiment dimensional element may include an emotional dimension. As used in this disclosure an "emotional dimension" is a dimension of wellness representing an individual's awareness and/or acceptance of feelings. For example, and without limitation, emotional dimension may include a dimension associated with an individual's feelings related to a belief, philosophy, behavior, and the like thereof.

Still referring to FIG. 2, computing device 104 may receive conduct indicator 204 as a function of obtaining an exposure element. As used in this disclosure an "exposure element" is an element of datum representing contact and/or exposure associated with a lifestyle. For example, and without limitation exposure element may denote prolonged contact to radioactive material as a function of being a nuclear power plant technician. As a further non-limiting example exposure element may denote prolonged contact to illicit drugs as a function of being a recreational drug user. As a further non-limiting example, exposure element may denote prolonged contact to heavy metals in water as a function of having a surfing lifestyle. In an embodiment, and without limitation, exposure element may denote one or more exposures to toxins such as, but not limited to, persistent organic pollutants, polychlorinated bisphenols, hydrogen chlorides, benzenes, xylenes, toluenes, dioxins, heavy metals, radioactivity, and the like thereof. In another embodiment, exposure element may denote one or more epigenetic factors. As used in this disclosure an "epigenetic factor" is a factor denoting a likelihood of a change in gene activity and/or expression as a function of one or more external factors. For example, and without limitation, epigenetic factor may denote a high likelihood for a gene mutation as a function of a polyaromatic hydrocarbon. As a further non-limiting example, epigenetic factor may denote a high likelihood for reduced gene expression as a function of aluminum toxicity and/or poisoning.

Still referring to FIG. 2, computing device 104 is configured to identify a functional signature 208 as a function of conduct indicator 204. As used in this disclosure a "functional signature" is a profile representing an individual's relative measure of wellness. For example and without limitation, functional signature 208 may represent that an individual has conduct indicators relating to a "healthy" and/or excellent wellness state. As a further non-limiting example, functional signature 208 may represent that an individual has conduct indicators relating to an "unhealthy" and/or poor wellness state. Functional signature 208 may be identified as a function of obtaining a salubrious reference 212. As used in this disclosure a "salubrious reference" is a guideline and/or recommendation representing an ideal health level of an individual. For example, and without limitation salubrious reference 212 may include a guideline that a blood pressure should be 120/80 mmHg. As a further non-limiting example, salubrious reference 212 may include a recommendation that a respiratory rate should be 14 breaths per minute. As a further non-limiting example, salubrious reference 212 may denote that an individual should exercise for 30 minutes every other day. As a further non-limiting example, salubrious reference 212 may denote that an individual should attend a religious gathering once a week. As a further non-limiting example, salubrious reference 212 may denote that an individual should meditate twice a day for 10 minutes. As a further non-limiting example, salubrious reference 212 may denote that an individual should have 5 or more chakras balanced during a particular time period, wherein a time period includes milliseconds, seconds, minutes, hours, days, weeks, months, years, and the like thereof. Salubrious reference 212 may be obtained as a function of one or more informed advisors, wherein an informed advisor is described above in detail. Additionally or alternatively, salubrious reference 212 may be obtained as a function of one or more functional advisors. As used in this disclosure a "functional advisor" is an individual capable of recommending and/or guiding an individual towards a more suited wellness state. For example, and without limitation, functional advisor may include one or more nutritionists, personal trainers, physical therapists, spiritual leaders, religious leaders, massage therapists, spiritual therapists, reiki masters, acupuncturists, life coaches, priests, philosophers, theologists, yoga instructors, wellness instructors, teachers, and the like thereof. In an embodiment, salubrious reference 212 may include recommendations from one or more medical sources such as peer reviews, informed advisor associations, medical web sites, medical textbooks, religious books, prophecies, spiritual texts, and the like thereof.

Still referring to FIG. 2, computing device 104 identifies functional signature 208 as function of salubrious reference 212 and conduct indicator 204 using a functional machine-learning model 216. As used in this disclosure a "functional machine-learning model" is a machine-learning model that produces a functional signature output given salubrious references and conduct indicators as inputs; this is in contrast to a non-machine learning software program where the commands to be executed are determined in advance by a user and written in a programming language. Functional machine-learning model may include one or more functional machine-learning processes such as supervised, unsupervised, or reinforcement machine-learning processes that computing device 104 and/or a remote device may or may not use in the determination of functional signature 208, wherein a remote device is an external device to computing device 104 as described above in detail. A functional machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 2, computing device 104 may train functional machine-learning process as a function of a functional training set. As used in this disclosure a "functional training set" is a training set that correlates at least salubrious reference 212 and conduct indicator 204 to a functional signature. For example, and without limitation, a salubrious reference of strenuous exercise for 1 hour per week and a conduct indicator associated with a running lifestyle may relate to a functional signature of a relatively "healthy" wellness state. The functional training set may be received as a function of user-entered valuations of salubrious references, conduct indicators, and/or functional signatures. Computing device 104 may receive functional training set by receiving correlations of salubrious references and/or conduct indicators that were previously received and/or determined during a previous iteration of determining functional signatures. The functional training set may be received by one or more remote devices that at least correlate a salubrious reference and conduct indicator to a functional signature, wherein a remote device is an external device to computing device 104, as described above. Functional training set may be received in the form of one or more user-entered correlations of a salubrious reference and/or conduct indicator to a functional signature. Additionally or alternatively, a user may include, without limitation, an informed advisor and/or a functional advisor entering correlations of salubrious references and/or conduct indicators to functional signatures, wherein informed advisors and/or functional advisors may include, without limitation, physicians, nutritionists, therapists, spiritual leaders, and the like thereof as described above in detail.

Still referring to FIG. 2, computing device 104 may receive functional machine-learning model 216 from a remote device that utilizes one or more functional machine learning processes, wherein remote device is described above in detail. For example, and without limitation, remote device may include a computing device, external device, processor, and the like thereof. Remote device may perform the functional machine-learning process using the functional training set to generate functional signature 208 and transmit the output to computing device 104. Remote device may transmit a signal, bit, datum, or parameter to computing device 104 that at least relates to functional signature 208. Additionally or alternatively, the remote device may provide an updated machine-learning model. For example, and without limitation, an updated machine-learning model may be comprised of a firmware update, a software update, a functional machine-learning process correction, and the like thereof. As a non-limiting example a software update may incorporate a new salubrious reference that relates to a modified conduct indicator. Additionally or alternatively, the updated machine learning model may be transmitted to the remote device, wherein the remote device may replace the functional machine-learning model with the updated machine-learning model and determine the physiological as a function of the conduct indicator using the updated machine-learning model. The updated machine-learning model may be transmitted by the remote device and received by computing device 104 as a software update, firmware update, or corrected functional machine-learning model. For example, and without limitation a functional machine-learning model 216 may utilize a neural net machine-learning process, wherein the updated machine-learning model may incorporate polynomial regression machine-learning process. Updated machine learning model may additionally or alternatively include any machine-learning model used as an updated machine learning model as described in U.S. Non-provisional application Ser. No. 17/106,658, filed on Nov. 30, 2020, and entitled "A SYSTEM AND METHOD FOR GENERATING A DYNAMIC WEIGHTED COMBINATION," the entirety of which is incorporated herein by reference. In an embodiment, and without limitation, functional machine-learning model 216 may identify functional signature 208 as a function of one or more classifiers, wherein a classifier is described above in detail.

Still referring to FIG. 2, computing device 104 may identify functional signature 208 by producing an indicator index as a function of conduct indicator 204. As used in this disclosure an "indicator index" is a measurable value associated with a conduct indicator. For example and without limitation, an indicator index may be 20 for a conduct indicator associated with meditating 3 times a day for 5 minutes. As a further non-limiting example, an indicator index may be 73 for a conduct indicator associated with a sedentary lifestyle comprising sitting down for 12 hours a day. In an embodiment, computing device may produce a weighted index as a function of the indicator index and procreant disorder. As used in this disclosure a "weighted index" is a weighted value associated with conduct indicator and procreant disorder. For example, and without limitation, a conduct indicator of a lifestyle of wearing tight clothing may relate to a value of 12 for men, wherein a procreant disorder for infertility may weight and/or alter the value to adjust to 21. For example, and without limitation, a conduct indicator of smoking tobacco for 30 years may be associated with a value of 74, wherein the value may be weighted to 81 as a function of an ectopic pregnancy.

Still referring to FIG. 2, computing device 104 may identify functional signature 208 as a function of determining a root cause. As used in this disclosure a "root cause" is a source of origination of a conduct indicator. For example, and without limitation, root cause may denote that an individual has a sedentary lifestyle as a function of watching television. As a further non-limiting root cause may denote that an individual started smoking as a function of a lack of religious guidance and/or spiritual teaching. As a further non-limiting example, root cause may denote that an individual has emotional instability as a function of one or more traumatic experiences and/or psychological traumas. Additionally or alternatively, computing device may determine a habit as a function of conduct indicator 204. As used in this disclosure a "habit" is a tendency and/or regularly practiced behavior that an individual exhibits. For example, and without limitation a habit may include swearing, trichotillomania, picking an individual's nose, smoking cigarettes, biting fingernails, drinking coffee, drinking tea, hair picking, watching television, eating fast food, alcohol, emotional shopping, social media use, drinking soda, eating chocolate, humming, sleeping-in, lying, procrastinating, being unfriendly, and the like thereof.

Still referring to FIG. 2, computing device 104 is configured to generate a functional program 220 as a function of functional signature 208 and procreant appraisal 144. As used in this disclosure a "functional program" is a program and/or instruction to alter an individual's lifestyle to affect the procreant appraisal. For example, and without limitation, functional program 220 may include a program that instructs an individual to perform 10 minutes of strenuous exercise every day for 5 weeks. As a further non-limiting example, functional program 220 may include a program that instructs an individual to meditate for 1 minute every other week. As a further non-limiting example, functional program 220 may instruct an individual to go on a hike for 2 hours once a week. Additionally or alternatively, functional program 220 may include a nourishment program 160, wherein a nourishment program is described above in detail, in reference to FIG. 1. For example, and without limitation, functional program 220 may instruct an individual to consume a paleo diet. In an embodiment and without limitation, functional program 220 may include one or more instructions such as, but not limited to a first instruction to exercise and a second instruction of a nourishment program. Computing device 104 generates functional program 220 as a function of functional signature 208 and procreant appraisal 144 using a program machine-learning model 224. As used in this disclosure a "program machine-learning model" is a machine-learning model that produces a functional program output given functional signatures and procreant appraisals as inputs; this is in contrast to a non-machine learning software program where the commands to be executed are determined in advance by a user and written in a programming language. Program machine-learning model may include one or more program machine-learning processes such as supervised, unsupervised, or reinforcement machine-learning processes that computing device 104 and/ or a remote device may or may not use in the determination of functional program 220, wherein a remote device is an external device to computing device 104 as described above in detail. A program machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 2, computing device 104 may train program machine-learning process as a function of a program training set. As used in this disclosure a "program training set" is a training set that correlates at least functional signature 208 and procreant appraisal 144 to a functional program. For example, and without limitation, a functional signature of a habit of being exposed to radioactivity and a procreant appraisal associated with endometriosis may relate to a functional program of a reduced exposure to radioactivity, exercise for 30 minutes to aid in eliminating the toxin, and increased meditation to reduce inflammation. The program training set may be received as a function of user-entered valuations of functional signatures, procreant appraisals, and/or functional programs. Computing device 104 may receive program training set by receiving correlations of functional signatures and/or procreant appraisals that were previously received and/or determined during a previous iteration of determining functional programs. The program training set may be received by one or more remote devices that at least correlate a functional signature and procreant appraisal to a functional program, wherein a remote device is an external device to computing device 104, as described above. Program training set may be received in the form of one or more user-entered correlations of a functional signature and/or procreant appraisal to a functional program. Additionally or alternatively, a user may include, without limitation, an informed advisor and/or a functional advisor entering correlations of functional signatures and/or procreant appraisals to functional programs, wherein informed advisors and/or functional advisors may include, without limitation, physicians, nutritionists, therapists, spiritual leaders, and the like thereof as described above in detail.

Still referring to FIG. 2, computing device 104 may receive program machine-learning model 224 from a remote device that utilizes one or more program machine learning processes, wherein remote device is described above in detail. For example, and without limitation, remote device may include a computing device, external device, processor, and the like thereof. Remote device may perform the program machine-learning process using the program training set to generate functional program 220 and transmit the output to computing device 104. Remote device may transmit a signal, bit, datum, or parameter to computing device 104 that at least relates to functional program 220. Additionally or alternatively, the remote device may provide an updated machine-learning model. For example, and without limitation, an updated machine-learning model may be comprised of a firmware update, a software update, a program machine-learning process correction, and the like thereof. As a non-limiting example a software update may incorporate a new functional signature that relates to a modified procreant appraisal. Additionally or alternatively, the updated machine learning model may be transmitted to the remote device, wherein the remote device may replace the program machine-learning model with the updated machine-learning model and determine the physiological as a function of the procreant appraisal using the updated machine-learning model. The updated machine-learning model may be transmitted by the remote device and received by computing device 104 as a software update, firmware update, or corrected program machine-learning model. For example, and without limitation a program machine-learning model 224 may utilize a neural net machine-learning process, wherein the updated machine-learning model may incorporate polynomial regression machine-learning process. Updated machine learning model may additionally or alternatively include any machine-learning model used as an updated machine learning model as described in U.S. Nonprovisional application Ser. No. 17/106,658, filed on Nov. 30, 2020, and entitled "A SYSTEM AND METHOD FOR GENERATING A DYNAMIC WEIGHTED COMBINATION," the entirety of which is incorporated herein by reference. In an embodiment, and without limitation, program machine-learning model 224 may identify functional program 220 as a function of one or more classifiers, wherein a classifier is described above in detail.

Still referring to FIG. 2, computing device 104 may generate functional program 220 as a function of determining a holistic prospect. As used in this disclosure a "holistic prospect" is a potential adjustment to an individual's functional signature. For example, and without limitation, holistic project may denote that a potential adjustment may include adjusting the amount of exercise and/or strenuous activity performed by the individual. As a further non-limiting example, holistic project may denote that a potential adjustment may include adjusting the amount of religious guidance that an individual receives. As a further non-limiting example, holistic project may denote that a potential adjustment may include adjusting the amount of chakra flow of an individual. As a further non-limiting example, holistic project may denote that a potential adjustment may include adjusting the number of social interactions that an individual experiences each day. As a further non-limiting example, holistic prospect may include a potential adjustment to a nourishment program through the alteration of one or more edibles and/or supplementation of a nourishment program. In an embodiment, holistic prospect may include one or more supplements. For example, and without limitation, a supplement may include vitamin E, linoleic acid, lipoic acid, inositol, magnesium, biotin, progestin, vitamin D, and the like thereof.

Still referring to FIG. 2, computing device 104 generate functional program 220 as a function of a procreant functional goal. As used in this disclosure an "procreant functional goal" is a predicted goal and/or purposeful plan to modify functional signature 208 and/or procreant appraisal 144. As a non-limiting example, procreant functional goal may include a treatment goal. As used in this disclosure a "treatment goal" is a procreant functional goal that is designed to at least reverse and/or eliminate functional signature 208, procreant appraisal 144, and/or procreant disorder. As a non-limiting example, a treatment goal may include reversing the effects of endometriosis as a function of exercise, diet, and/or supplementation. As a further non-limiting example, a treatment goal includes reversing polycystic ovary syndrome as a function of recommending the supplement N-acetyl cysteine, recommending edibles such as licorice, flaxseed, saw palmetto, cinnamon, fenugreek, milk thistle, chasteberry, and/or dandelion root, recommending a meditation schedule of once per day for 20 minutes, and/or recommending 25 minutes of exercise every other day. Procreant functional goal may include a prevention goal. As used in this disclosure a "prevention goal" is a procreant functional goal that is designed to at least prevent and/or avert functional signature 208, procreant appraisal 144, and/or procreant disorder. As a non-limiting example, a prevention goal may include preventing the development of the infertility as a function of hiking 2 miles per day and/or recommending a nourishment program of a low-carb diet. Procreant functional goal may include a mitigation goal. As used in this disclosure a "mitigation goal" is a functional goal that is designed to reduce the symptoms and/or effects of a procreant disorder. For example, and without limitation, mitigation goal may include reducing the effects of Lynch syndrome as a function of recommending magnesium and/or zinc supplements and/or recommending enhanced chakra flow of an individual's body. Additionally or alternatively, procreant functional goal may include one or more goals associated with gene therapy to alter and/or mutate an individual's epigenetic factors.

Still referring to FIG. 2, computing device 104 may generate functional program 220 as a function of functional signature 208 and procreant functional goal using a goal machine-learning model. As used in this disclosure a "goal machine-learning model" is a machine-learning model to produce a functional program output given functional signatures and/or procreant functional goals as inputs; this is in contrast to a non-machine learning software program where the commands to be executed are determined in advance by a user and written in a programming language. Goal machine-learning model may include one or more goal machine-learning processes such as supervised, unsupervised, or reinforcement machine-learning processes that computing device 104 and/or a remote device may or may not use in the development of functional program 220. Goal machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 2, computing device 104 may train goal machine-learning process as a function of a goal training set. As used in this disclosure a "goal training set" is a training set that correlates a procreant functional goal to a functional signature. The goal training set may be received as a function of user-entered functional signatures, procreant functional goals, and/or functional programs. For example, and without limitation, a procreant functional goal of treating uterine fibroids may correlate to a functional signature of physical activity and/or a vegan diet. Computing device 104 may receive goal training by receiving correlations of procreant functional goals and/or functional signatures that were previously received and/or determined during a previous iteration of generating functional programs. The goal training set may be received by one or more remote devices that at least correlate a procreant functional goal and/or functional signature to a functional program, wherein a remote device is an external device to computing device 104, as described above. Goal training set may be received in the form of one or more user-entered correlations of a procreant functional goal and/or functional signature to a functional program. Additionally or alternatively, a user may include, without limitation, an informed advisor and/or a functional advisor entering correlations of functional signatures and/or procreant appraisals to functional programs, wherein informed advisors and/or functional advisors may include, without limitation, physicians, nutritionists, therapists, spiritual leaders, and the like thereof as described above in detail.

Still referring to FIG. 2, computing device 104 may receive goal machine-learning model from the remote device that utilizes one or more goal machine learning processes, wherein a remote device is described above in detail. For example, and without limitation, a remote device may include a computing device, external device, processor, and the like thereof. The remote device may perform the goal machine-learning process using the goal training set to develop functional program 220 and transmit the output to computing device 104. The remote device may transmit a signal, bit, datum, or parameter to computing device 104 that at least relates to functional program 220. Additionally or alternatively, the remote device may provide an updated machine-learning model. For example, and without limitation, an updated machine-learning model may be comprised of a firmware update, a software update, a goal machine-learning process correction, and the like thereof. As a non-limiting example a software update may incorporate a new procreant functional goal that relates to a modified functional signature. Additionally or alternatively, the updated machine learning model may be transmitted to the remote device, wherein the remote device may replace the goal machine-learning model with the updated machine-learning model and develop the functional program as a function of the procreant functional goal using the updated machine-learning model. The updated machine-learning model may be transmitted by the remote device and received by computing device 104 as a software update, firmware update, or corrected goal machine-learning model. For example, and without limitation goal machine-learning model may utilize a neural net machine-learning process, wherein the updated machine-learning model may incorporate decision tree machine-learning processes.

Figure 3:
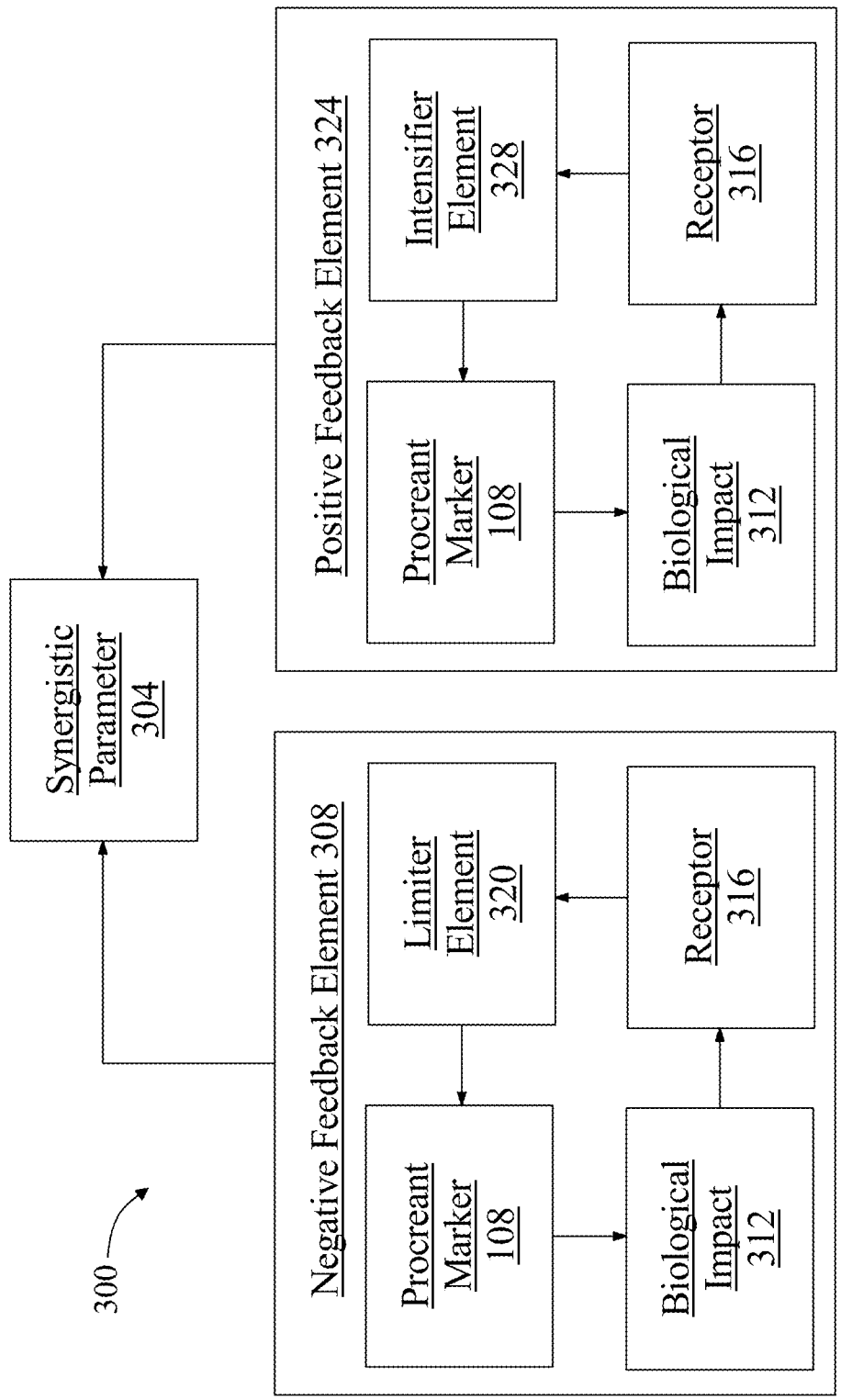
FIG. 3 is a representative diagram of an exemplary embodiment of synergistic parameters according to an embodiment of the invention.

Now referring to FIG. 3, an exemplary embodiment 300 of a synergistic parameter 304 according to an embodiment of the invention is illustrated. As used in this disclosure "synergistic parameter" is a parameter that identifies one or more additional biomarkers that contribute to the same function in the human body. As a non-limiting example a synergistic parameter may be identified for the biomarkers such as 25-hydroxyvitamin D, vitamin D binding protein, and parathyroid hormone, wherein each of the biomarkers relate to the absorption and regulation of vitamin D. Synergistic parameter 304 may include a negative feedback element 308. As used in this disclosure "negative feedback element" is an element that reduces the output of the input. As a non-limiting example negative feedback element may relate to an input of the biomarker glucose, wherein the output is insulin, such that the glucose is reduced. Negative feedback element 308 may receive procreant marker 108 and identify a biological impact 312. As used in this disclosure "biological impact" is an effect that a procreant marker has on the procreant system of an individual. As a non-limiting example, biological impact 312 may include an impact associated with an increase of testosterone in the procreant system. Biological impact 312 may be determined as a function of a receptor 316. As used in this disclosure "receptor" is a special structure found in procreant system that at least binds to specialized molecules using a lock and key mechanism. As a non-limiting examples receptor 316 may include estrogen receptors, CB2 receptors, testosterone receptors, endocannabinoid receptors, and the like thereof. Negative feedback element 308 may determine a limiter element 320 as a function of receptor 316. As used in this disclosure "limiter element" is an element that reduces and/or minimizes procreant marker 108. As a non-limiting example a limiter element may include gonadotropin-releasing hormone, wherein gonadotropin-releasing hormone may inhibit the production of estrogen. Synergistic parameter 304 may include a positive feedback element 324. As used in this disclosure "positive feedback element" is an element that enhances the output of the input. As a non-limiting example positive feedback element may include childbirth, wherein pressure on the cervix stimulates the release of oxytocin, which stimulates further contractions and additional pressure on the cervix. Positive feedback element 324 may include biological input 312 as described in detail above. Positive feedback element 324 may include receptor 316 as described above in detail. Positive feedback element 324 may determine an intensifier element 328 as a function of receptor 316. As used in this disclosure "intensifier element" is an element that enhances and/or maximizes procreant marker 108. As a non-limiting example intensifier element 328 may include TF:VII activation by FXa, wherein FXa enhances the activation and/or production of TF:VII to produce more blood clotting.

Figure 4:
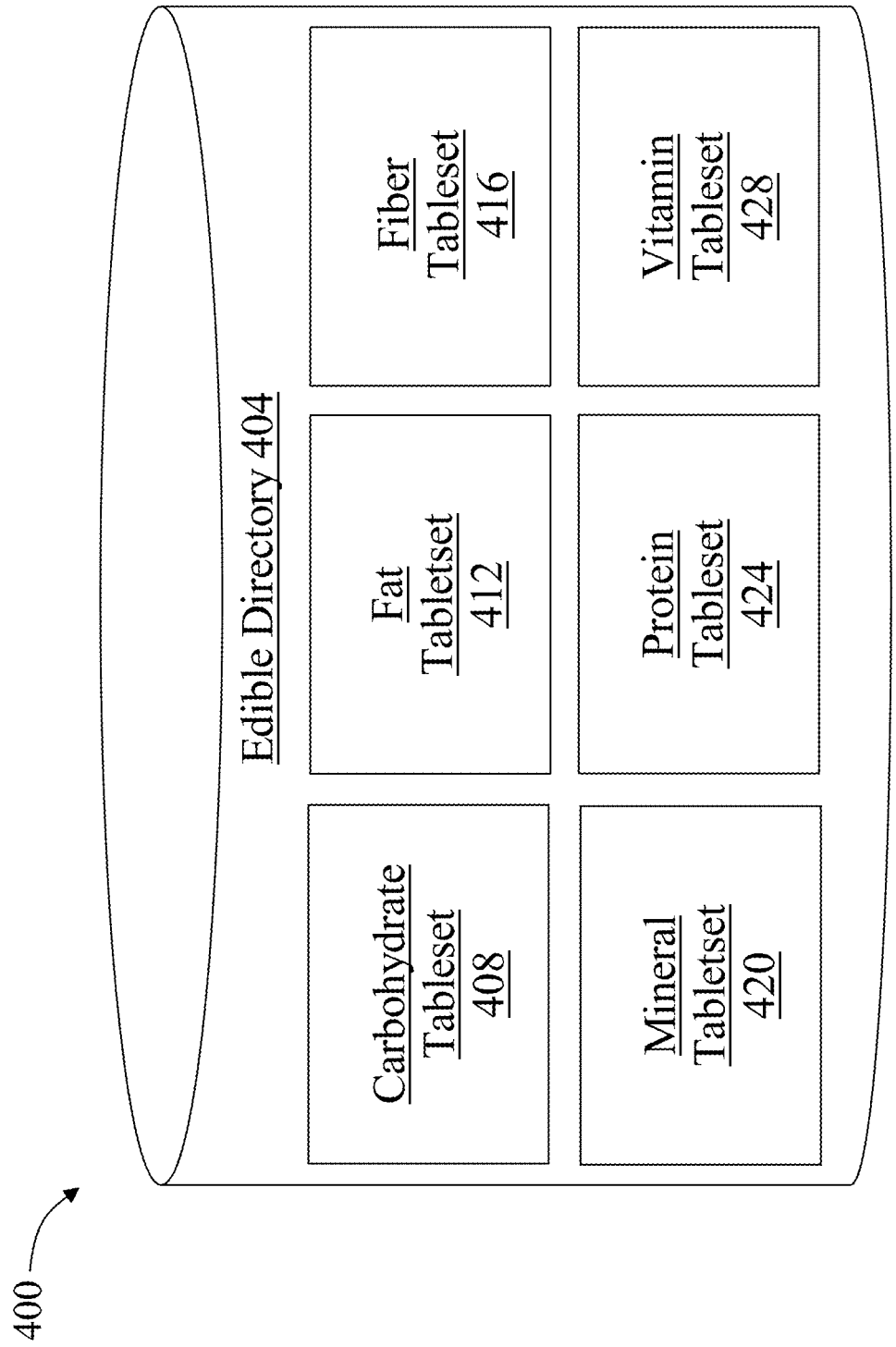
FIG. 4 is a block diagram of an exemplary embodiment of an edible directory according to an embodiment of the invention.

Now referring to FIG. 4, an exemplary embodiment 400 of an edible directory 404 according to an embodiment of the invention is illustrated. Edible directory 404 may be implemented, without limitation, as a relational databank, a key-value retrieval databank such as a NOSQL databank, or any other format or structure for use as a databank that a person skilled in the art would recognize as suitable upon review of the entirety of this disclosure. Edible directory 404 may alternatively or additionally be implemented using a distributed data storage protocol and/or data structure, such as a distributed hash table or the like. Edible directory 404 may include a plurality of data entries and/or records as described above. Data entries in a databank may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a databank may store, retrieve, organize, and/or reflect data and/or records as used herein, as well as categories and/or populations of data consistently with this disclosure. Edible directory 404 may include a carbohydrate tableset 408. Carbohydrate tableset 408 may relate to a nourishment composition of an edible with respect to the quantity and/or type of carbohydrates in the edible. As a non-limiting example, carbohydrate tableset 408 may include monosaccharides, disaccharides, oligosaccharides, polysaccharides, and the like thereof. Edible directory 404 may include a fat tableset 412. Fat tableset 412 may relate to a nourishment composition of an edible with respect to the quantity and/or type of esterified fatty acids in the edible. Fat tableset 412 may include, without limitation, triglycerides, monoglycerides, diglycerides, phospholipids, sterols, waxes, and free fatty acids. Edible directory 404 may include a fiber tableset 416. Fiber tableset 416 may relate to a nourishment composition of an edible with respect to the quantity and/or type of fiber in the edible. As a non-limiting example, fiber tableset 416 may include soluble fiber, such as beta-glucans, raw guar gum, psyllium, inulin, and the like thereof as well as insoluble fiber, such as wheat bran, cellulose, lignin, and the like thereof. Edible directory 404 may include a mineral tableset 420. Mineral tableset 420 may relate to a nourishment composition of an edible with respect to the quantity and/or type of minerals in the edible. As a non-limiting example, mineral tableset 420 may include calcium, phosphorous, magnesium, sodium, potassium, chloride, sulfur, iron, manganese, copper, iodine, zing, cobalt, fluoride, selenium, and the like thereof. Edible directory 404 may include a protein tableset 424. Protein tableset 424 may relate to a nourishment composition of an edible with respect to the quantity and/or type of proteins in the edible. As a non-limiting example, protein tableset 424 may include amino acids combinations, wherein amino acids may include, without limitation, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, and the like thereof. Edible directory 404 may include a vitamin tableset 428. Vitamin tableset 428 may relate to a nourishment composition of an edible with respect to the quantity and/or type of vitamins in the edible. As a non-limiting example, vitamin tableset 428 may include vitamin A, vitamin $B_1$, vitamin $B_2$, vitamin $B_3$, vitamin $B_5$, vitamin $B_6$, vitamin $B_7$, vitamin $B_9$, vitamin $B_{12}$, vitamin C, vitamin D, vitamin E, vitamin K, and the like thereof.

Figure 5:
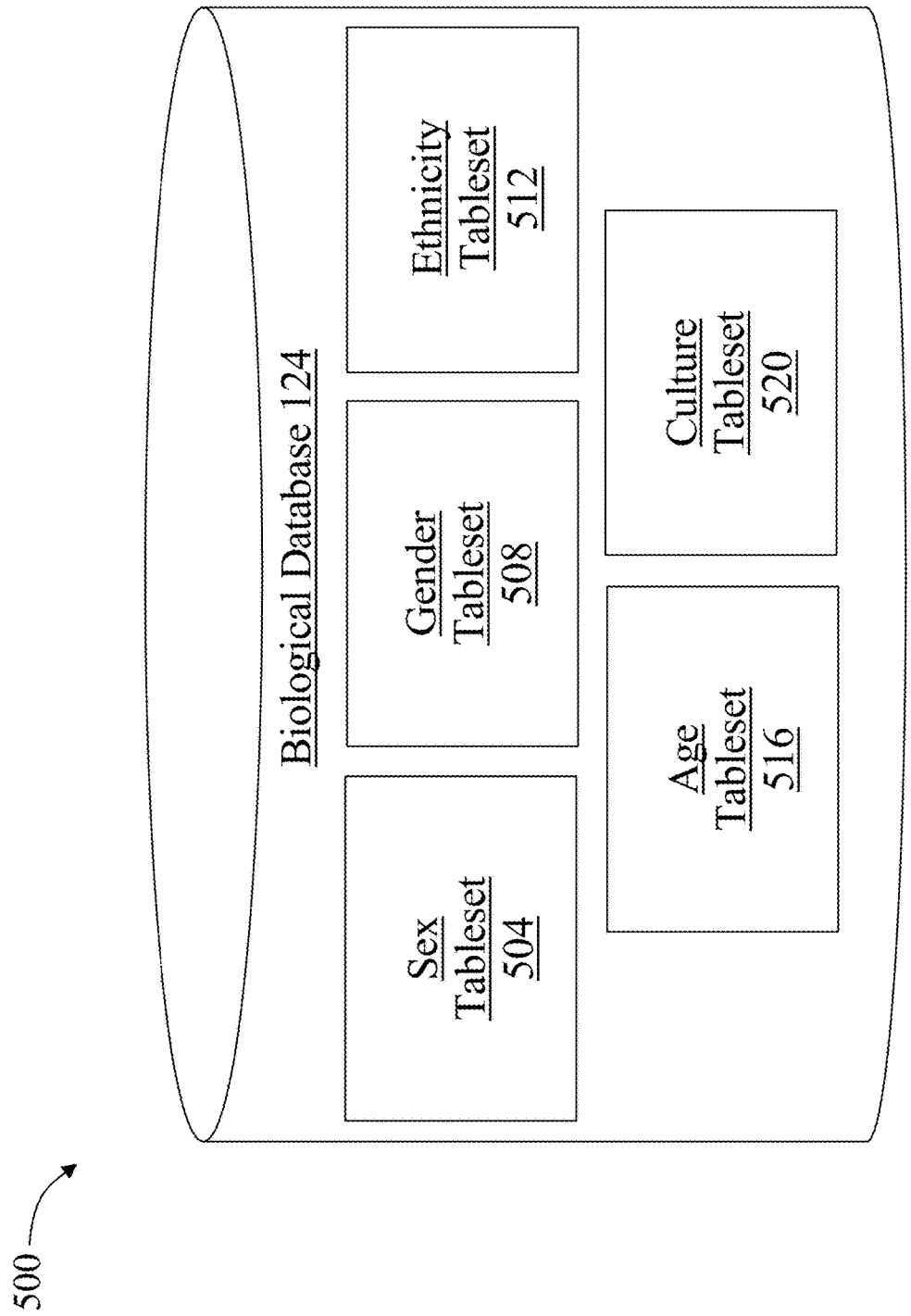
FIG. 5 is a block diagram of an exemplary embodiment of a biological database according to an embodiment of the invention.

Now referring to FIG. 5, an exemplary embodiment 500 of a biological database 124 according to an embodiment of the invention is illustrated. Biological database 124 may be implemented, without limitation, as a relational databank, a key-value retrieval databank such as a NOSQL databank, or any other format or structure for use as a databank that a person skilled in the art would recognize as suitable upon review of the entirety of this disclosure. Biological database 124 may alternatively or additionally be implemented using a distributed data storage protocol and/or data structure, such as a distributed hash table or the like. Biological database 124 may include a plurality of data entries and/or records as described above. Data entries in a databank may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a databank may store, retrieve, organize, and/or reflect data and/or records as used herein, as well as categories and/or populations of data consistently with this disclosure. Biological database 124 may include a sex tableset 504. Sex tableset 504 may include one or more sex-specific biomarkers that distinguish one or more ilk parameters relating to the sex of a subject. As a non-limiting example, sex tableset 504 may include 51249_at (LPL: lipoprotein lipase), 41755_at (COBLL1: COBL-like 1), 39878_at (PCDH9: protocadherin 9), 38211_at (ZBTB20: zinc finger and BTB domain containing 20), 39488_at (PCDH9: protocadherin 9), 36886_f_at (KIR2DL3: killer cell immunoglobulin-like receptor, two domains, long cytoplasmic tail, 3), 32144_at (SORL1: sortilin-related receptor, L(DLR class) A repeats-containing), 33535_at (P2RX1: purinergic receptor P2X, ligand-gated ion channel, 1), 39967_at (LDOC1: leucine zipper, down-regulated in cancer 1), 42842__at (BCL7A: B-cell CLL/lymphoma 7A), 36899_at (SATB1: special AT-rich sequence binding protein 1 (binds to nuclear matrix/scaffold-associating DNA's)), 33745_at (PHKG2: phosphorylase kinase, gamma 2 (testis)), 38156_at (LOH11CR2A: loss of heterozygosity, 11, chromosomal region 2, gene A), 34142_at (PDE8A: phosphodiesterase 8A), 39593_at (FGL2: fibrinogen-like 2), and 217_at (KLK2: kallikrein 2, prostatic), and the like thereof. Biological database 124 may include a gender tableset 508. Gender tableset 508 may include one or more gender-specific biomarkers that distinguish one or more ilk parameters relating to the gender of a subject. As a non-limiting parameter gender tableset 508 may relate to the cortical thickness of a subject and/or the level of activation of the right superior frontal gyms. Biological database 124 may include an ethnicity tableset 512. Biological database 124 may include one or more ethnicity-specific biomarkers that distinguish one or more ilk parameters relating to the ethnicity of a subject. As a no-limiting example ethnicity tableset 512 may include NTproBNP, hsCRP, CysC, MPO, hsTnI, and the like thereof. Ethnicity tableset 516 may include an age tableset 516. Age tableset 516 may include one or more age-specific biomarkers that distinguish one or more ilk parameters relating to the age of a subject. As a non-limiting example age tableset 516 may include SBP, DBP, HDL ratio, cholesterol, triglycerides, HB1Ac, weight, height, BMI, waist circumference, hip circumference, creatine clearance, albumin, leukocyte count, IL-6, urinary cortisol, epinephrine, norepinephrine, dopamine, and the like thereof. Biological database 124 may include a culture tableset 520. Culture tableset 520 may include one or more culture-specific biomarkers that distinguish one or more ilk parameters relating to the culture of a subject. As a non-limiting example culture tableset 520 may include 3-methylindole, succinyl acetone, S-methyl-L-thiocitrulline, O-arachidonoyl glycidol, and the like thereof.

Figure 6:
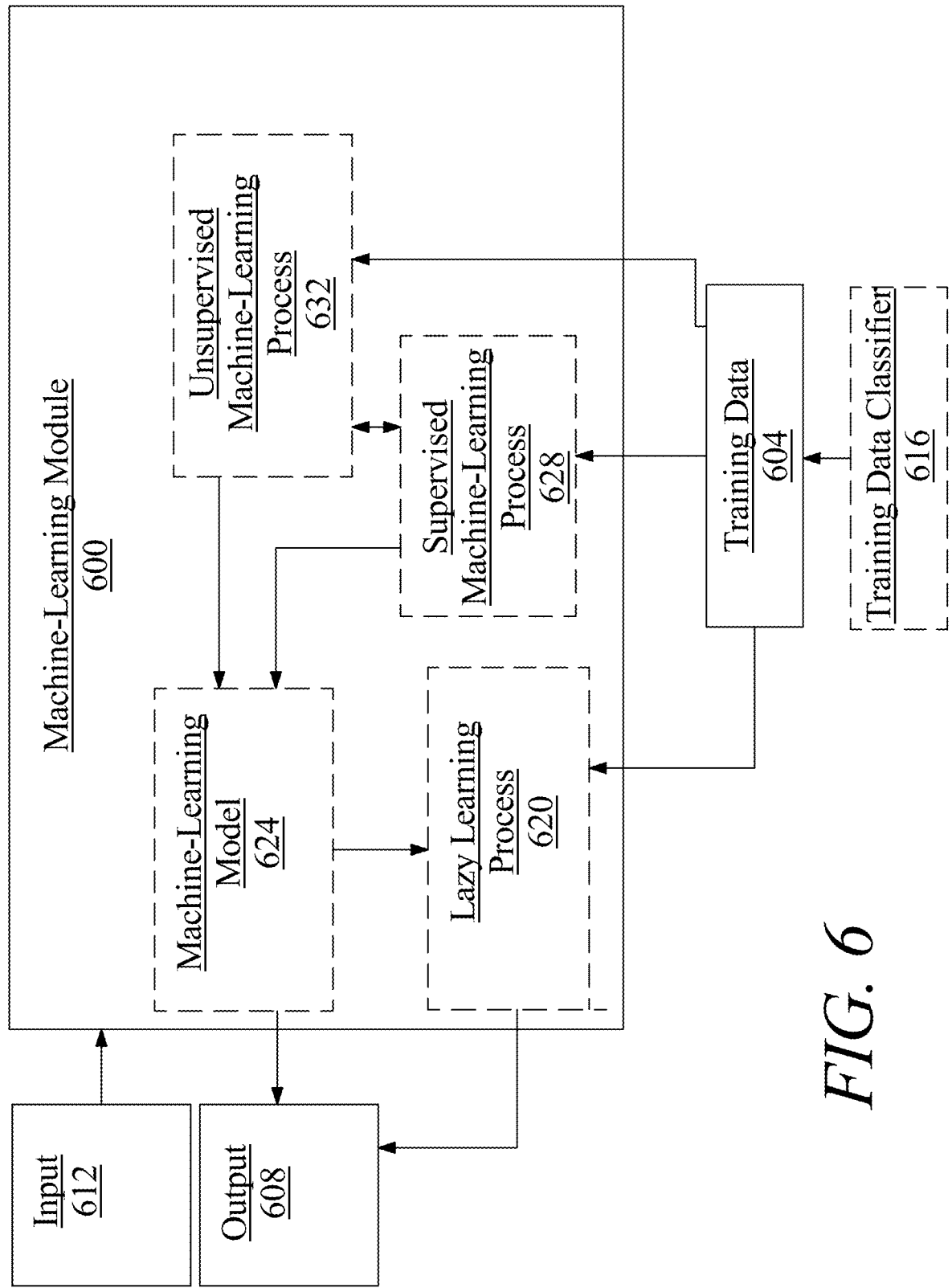
FIG. 6 is a block diagram of an exemplary embodiment of a machine-learning module.

Referring now to FIG. 6, an exemplary embodiment of a machine-learning module 600 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 604 to generate an algorithm that will be performed by a computing device/module to produce outputs 608 given data provided as inputs 612; this is in contrast to a non-machine learning software program where the commands to be executed are determined in advance by a user and written in a programming language.

Still referring to FIG. 6, "training data," as used herein, is data containing correlations that a machine-learning process may use to model relationships between two or more categories of data elements. For instance, and without limitation, training data 604 may include a plurality of data entries, each entry representing a set of data elements that were recorded, received, and/or generated together; data elements may be correlated by shared existence in a given data entry, by proximity in a given data entry, or the like. Multiple data entries in training data 604 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 604 according to various correlations; correlations may indicate causative and/or predictive links between categories of data elements, which may be modeled as relationships such as mathematical relationships by machine-learning processes as described in further detail below. Training data 604 may be formatted and/or organized by categories of data elements, for instance by associating data elements with one or more descriptors corresponding to categories of data elements. As a non-limiting example, training data 604 may include data entered in standardized forms by persons or processes, such that entry of a given data element in a given field in a form may be mapped to one or more descriptors of categories. Elements in training data 604 may be linked to descriptors of categories by tags, tokens, or other data elements; for instance, and without limitation, training data 604 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 6, training data 604 may include one or more elements that are not categorized; that is, training data 604 may not be formatted or contain descriptors for some elements of data. Machine-learning algorithms and/or other processes may sort training data 604 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 604 to be made applicable for two or more distinct machine-learning algorithms as described in further detail below. Training data 604 used by machine-learning module 600 may correlate any input data as described in this disclosure to any output data as described in this disclosure. As a non-limiting illustrative example inputs may include ilk parameters and/or procreant markers, wherein a procreant fascicle is outputted.

Further referring to FIG. 6, training data may be filtered, sorted, and/or selected using one or more supervised and/or unsupervised machine-learning processes and/or models as described in further detail below; such models may include without limitation a training data classifier 616. Training data classifier 616 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 600 may generate a classifier using a classification algorithm, defined as a processes whereby a computing device and/or any module and/or component operating thereon derives a classifier from training data 604. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 616 may classify elements of training data to sub-categories of ilk parameters including sex, gender, age, culture, and the like thereof.

Still referring to FIG. 6, machine-learning module 600 may be configured to perform a lazy-learning process 620 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 604. Heuristic may include selecting some number of highest-ranking associations and/or training data 604 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 6, machine-learning processes as described in this disclosure may be used to generate machine-learning models 624. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 624 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 624 may be generated by creating an artificial neural network, such as a convolutional neural network comprising an input layer of nodes, one or more intermediate layers, and an output layer of nodes. Connections between nodes may be created via the process of "training" the network, in which elements as a function of a training data 604 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 6, machine-learning algorithms may include at least a supervised machine-learning process 628. At least a supervised machine-learning process 628, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include ilk parameters and/or procreant markers as described above as inputs, procreant fascicles as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 604. Persons skilled in the art, upon reviewing the entirety of this disclosure, will be aware of various possible variations of at least a supervised machine-learning process 628 that may be used to determine relation between inputs and outputs. Supervised machine-learning processes may include classification algorithms as defined above.

Further referring to FIG. 6, machine learning processes may include at least an unsupervised machine-learning processes 632. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 6, machine-learning module 600 may be designed and configured to create a machine-learning model 624 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 6, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 7:
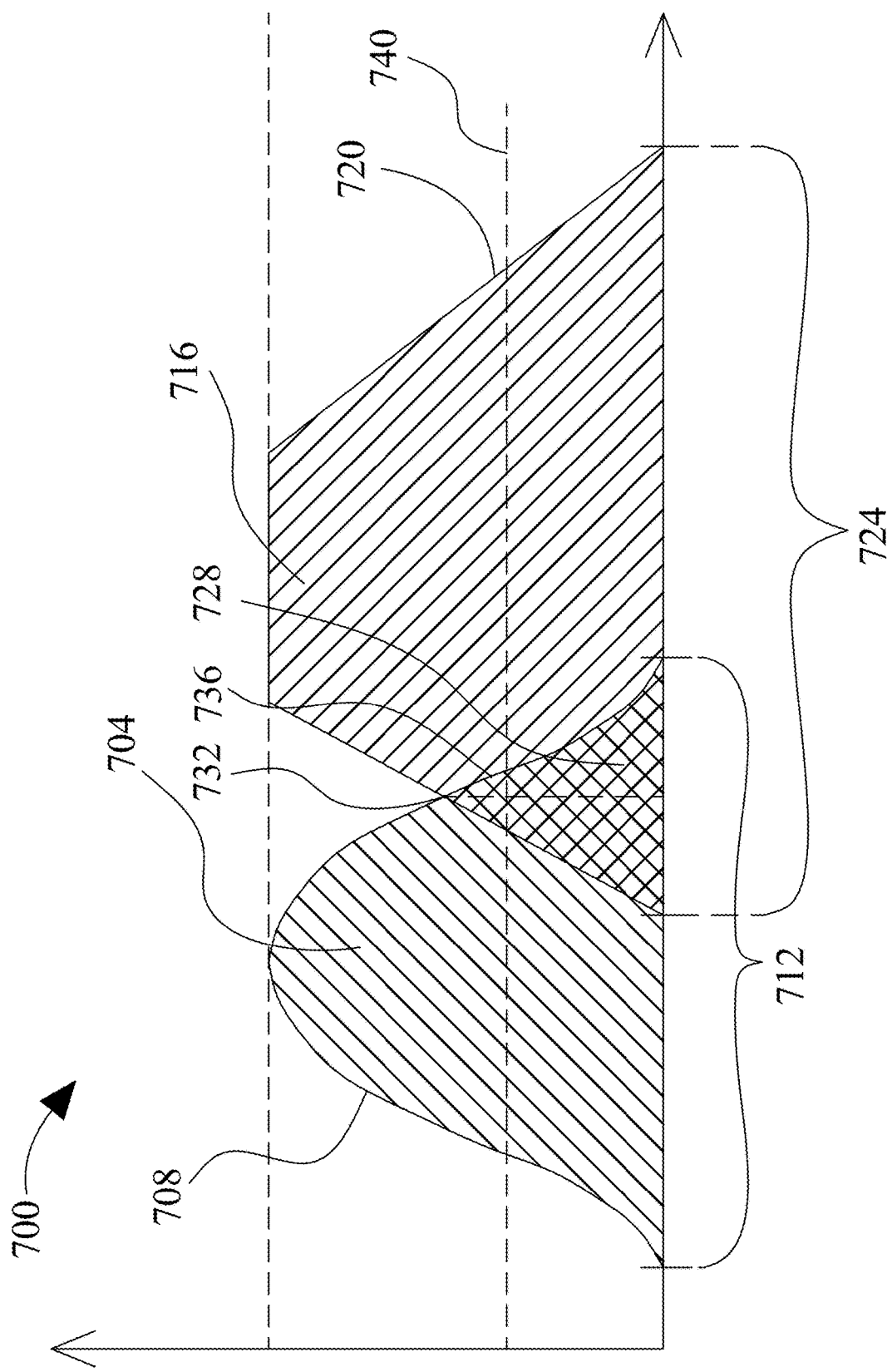
FIG. 7 is a block diagram of an exemplary embodiment of a safe range.

Referring now to FIG. 7, an exemplary embodiment of safe range 700 is illustrated. A first safe range 704 may be represented, without limitation, according to a first membership function 708 representing a probability that an input falling on a first range of values 712 is a member of the first safe range 704, where the first membership function 308 has values on a range of probabilities such as without limitation the interval [0,1], and an area beneath the first membership function 708 may represent a set of values within first safe range 704. Although first range of values 712 is illustrated for clarity in this exemplary depiction as a range on a single number line or axis, first range of values 712 may be defined on two or more dimensions, representing, for instance, a Cartesian product between a plurality of ranges, curves, axes, spaces, dimensions, or the like. First membership function 708 may include any suitable function mapping first range 712 to a probability interval, including without limitation a triangular function defined by two linear elements such as line segments or planes that intersect at or below the top of the probability interval. As a non-limiting example, triangular membership function may be defined as:

$$y(x, a, b, c) = \begin{cases} 0, \text{ for } x > c \text{ and } x < a \\ \frac{x-a}{b-a}, \text{ for } a \leq x < b \\ \frac{c-x}{c-b}, \text{ if } b < x \leq c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}(\frac{x-c}{\sigma})^2}$$

and a bell membership function may be defined as:

$$y(x, a, b, c,) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

Still referring to FIG. 7, first safe range 704 may represent any value or combination of values as described above, including procreant enumeration 136, any resource datum, any niche datum, and/or any combination of the above. A second safe range 716, which may represent any value which may be represented by first safe range 704, may be defined by a second membership function 720 on a second range 724; second range 724 may be identical and/or overlap with first range 712 and/or may be combined with first range via Cartesian product or the like to generate a mapping permitting evaluation overlap of first fuzzy set 704 and second safe range 716. Where first safe range 704 and second safe range 716 have a region 728 that overlaps, first membership function 708 and second membership function 720 may intersect at a point 732 representing a probability, as defined on probability interval, of a match between first safe range 704 and second safe range 716. Alternatively or additionally, a single value of first and/or second fuzzy set may be located at a locus 736 on first range 712 and/or second range 724, where a probability of membership may be taken by evaluation of first membership function 708 and/or second membership function 720 at that range point. A probability at 728 and/or 732 may be compared to a threshold 740 to determine whether a positive match is indicated. Threshold 740 may, in a non-limiting example, represent a degree of match between first safe range 704 and second safe range 716, and/or single values therein with each other or with either set, which is sufficient for purposes of the matching process; for instance, threshold may indicate a sufficient degree of overlap between procreant enumeration 136 and output procreant appraisal 144 for combination to occur as described above. Each threshold may be established by one or more procreant recommendations 152. Alternatively or additionally, each threshold may be tuned by a machine-learning and/or statistical process, for instance and without limitation as described in further detail below.

Figure 8:
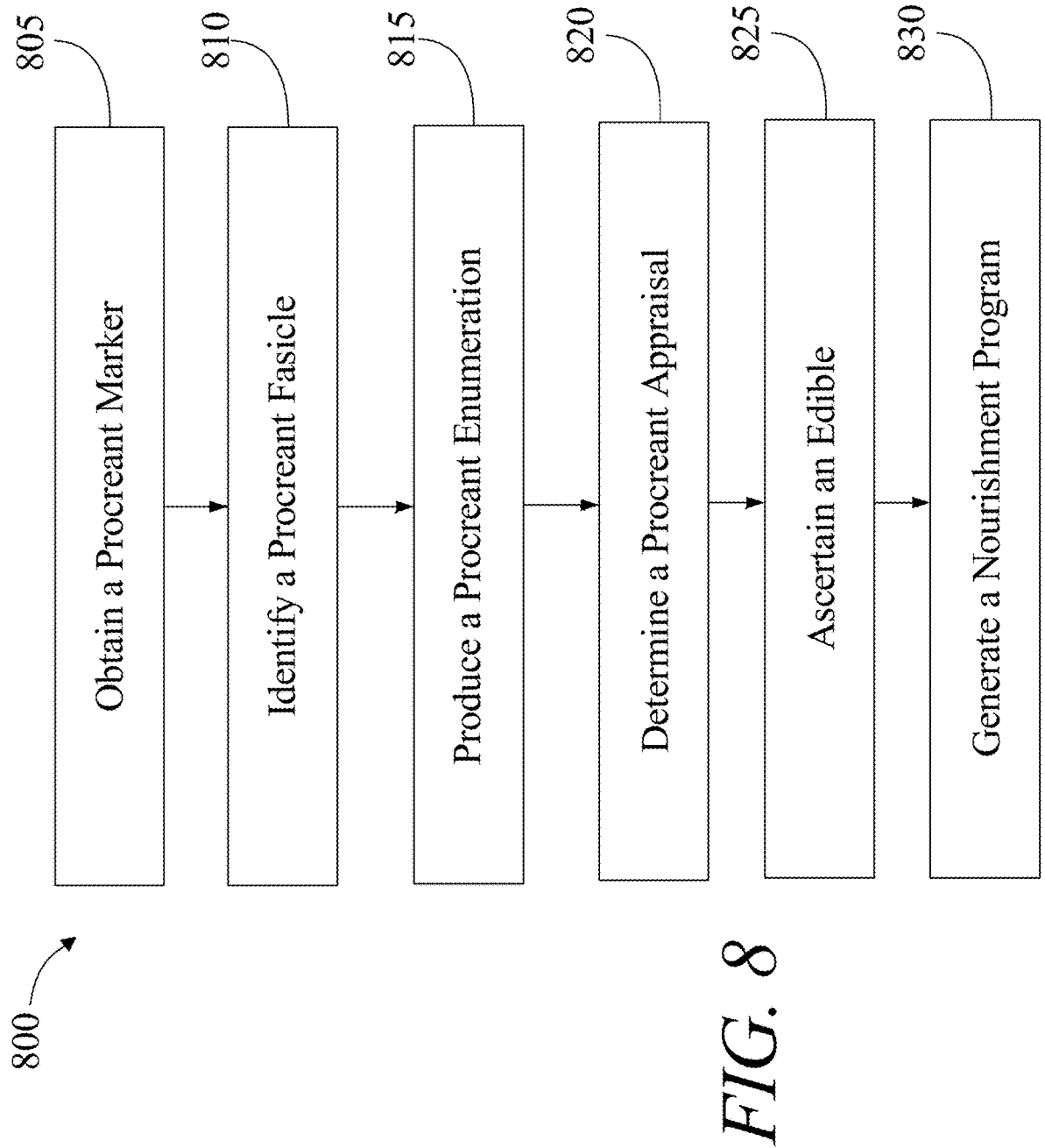
FIG. 8 is a process flow diagram illustrating an exemplary embodiment of a method of generating a procreant nourishment program.

Now referring to FIG. 8 an exemplary embodiment of a method 800 for generating a procreant nourishment program is illustrated. At step 805, a computing device 104 obtains at least a procreant marker 108 as a function of a procreant system 112. Computing device 104 includes any of the computing device 104 as described above, in reference to FIGS. 1-7. Procreant marker 108 includes any of the procreant marker 108 as described above, in reference to FIGS. 1-7. Procreant system 112 includes any of the procreant system 112 as described above, in reference to FIGS. 1-7.

Still referring to FIG. 8, at step 810, computing device 104 identifies a procreant fascicle 116 as a function of procreant marker 108. Procreant fascicle 116 includes any of the procreant fascicle 116 as described above, in reference to FIGS. 1-7. Computing device 104 receives an ilk parameter 120 as a function of a biological database 124. Ilk parameter 120 includes any of the ilk parameter 120 as described above, in reference to FIGS. 1-7. Biological database 124 includes any of the biological database 124 as described above, in reference to FIGS. 1-7. Computing device 104 retrieves at least a procreant functional goal 128. Functional goal 128 includes any of the functional goal 128 as described above, in reference to FIGS. 1-7. Computing device identifies procreant fascicle 116 as a function of ilk parameter 120, procreant functional goal 128, and procreant marker 108 using a procreant machine-learning model 132. Procreant machine-learning model 132 includes any of the procreant machine-learning model 132 as described above, in reference to FIGS. 1-7.

Still referring to FIG. 8, at step 815, computing device produces a procreant enumeration 136 using an enumeration machine-learning model 140. Procreant enumeration 136 includes any of the procreant enumeration 136 as described above, in reference to FIGS. 1-7. Enumeration machine-learning model 140 includes any of the enumeration machine-learning model as described above, in reference to FIGS. 1-7.

Still referring to FIG. 8, at step 820, computing device 104 determines a procreant appraisal 144 as a function of procreant enumeration 136. Procreant appraisal 144 includes any of the procreant appraisal 144 as described above, in reference to FIGS. 1-7. Computing device determines procreant appraisal 144 by receiving a safe range 148 as a function of a procreant recommendation 152. Safe range 148 includes any of the safe range 148 as described above, in reference to FIGS. 1-6. Procreant recommendation 152 includes any of the procreant recommendation 152 as described above, in reference to FIGS. 1-7.

Still referring to FIG. 8, at step 825, computing device 104 ascertains at least an edible 156 as a function of procreant appraisal 136. Edible 156 includes any of the edible 156 as described above, in reference to FIGS. 1-7.

Still referring to FIG. 8, at step 830, computing device 104, generates a nourishment program 160 of a plurality of nourishment programs as a function of edible 156. Nourishment program 160 includes any of the nourishment program 160 as described above, in reference to FIGS. 1-7.

Figure 9:
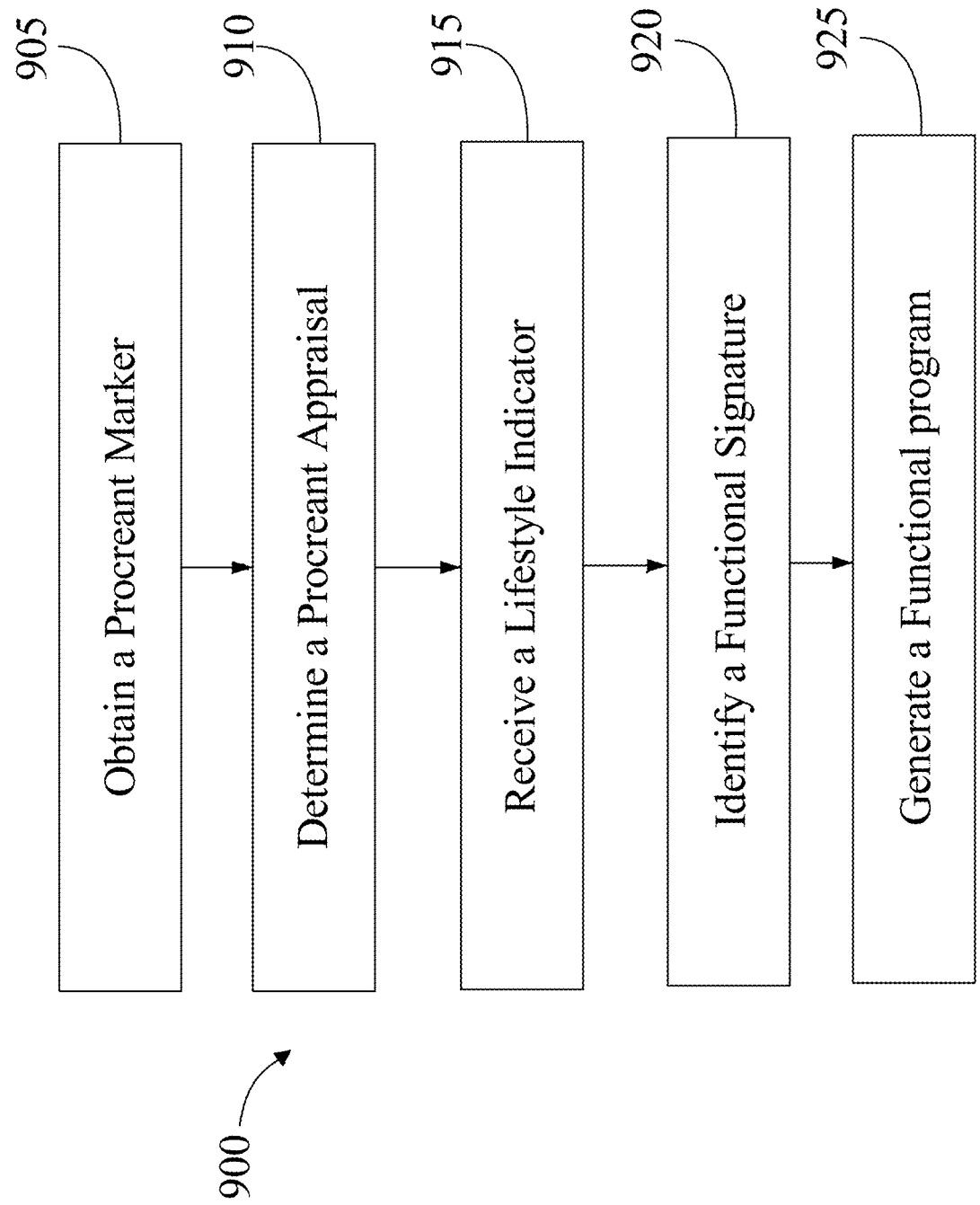
FIG. 9 is a process flow diagram illustrating an exemplary embodiment of a method of generating a procreant functional program.

Now referring to FIG. 9, an exemplary embodiment of a method 900 for generating a procreant functional program is illustrated. At step 905, a computing device 104 obtains a procreant marker 108 as a function of a procreant system 112. Computing device 104 includes any of the computing device 104 as described above, in reference to FIGS. 1-8. Procreant marker 108 includes any of the procreant marker 108 as described above, in reference to FIGS. 1-8. Procreant system 112 includes any of the procreant system 112 as described above, in reference to FIGS. 1-8.

Still referring to FIG. 9, at step 910, computing device 104 determines a procreant appraisal 144 as a function of procreant marker 108. Procreant appraisal 144 includes any of the procreant appraisal 144 as described above, in reference to FIGS. 1-8. Computing device 104 determines procreant appraisal 144 by producing a procreant enumeration 136 as a function of procreant marker 108. Procreant enumeration 136 includes any of the procreant enumeration 136 as described above, in reference to FIGS. 1-8. Computing device 104 determines procreant appraisal 144 as a function of procreant enumeration 136 and a safe range 148. Safe range 148 includes any of the safe range 148 as described above, in reference to FIGS. 1-8.

Still referring to FIG. 9, at step 915, computing device 104 receives a conduct indicator 204. Conduct indicator 204 includes any of the conduct indicator 204 as described above, in reference to FIGS. 1-8.

Still referring to FIG. 9, at step 925, computing device 104 identifies a functional signature 208 as a function of conduct indicator 204. Functional signature 208 includes any of the functional signature 208 as described above, in reference to FIGS. 1-8. Computing device 104 identifies functional signature 204 as a function of obtaining a salubrious reference 212. Salubrious reference 212 includes any of the salubrious reference 212 as described above, in reference to FIGS. 1-8. Computing device 104 identifies functional signature 208 as a function of conduct indicator 208 and salubrious reference 212 using a functional machine-learning model 216. Functional machine-learning model 216 includes any of the functional machine-learning model 216 as described above, in reference to FIGS. 1-8.

Still referring to FIG. 9, at step, 920, computing device 104 generates a functional program 216 as a function of functional signature 204 and procreant appraisal 144 using a program machine-learning model 224. Functional program 216 includes any of the functional program 216 as described above, in reference to FIGS. 1-8. Program machine-learning model 224 includes any of the program machine-learning model 224 as described above, in reference to FIGS. 1-8.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 10:
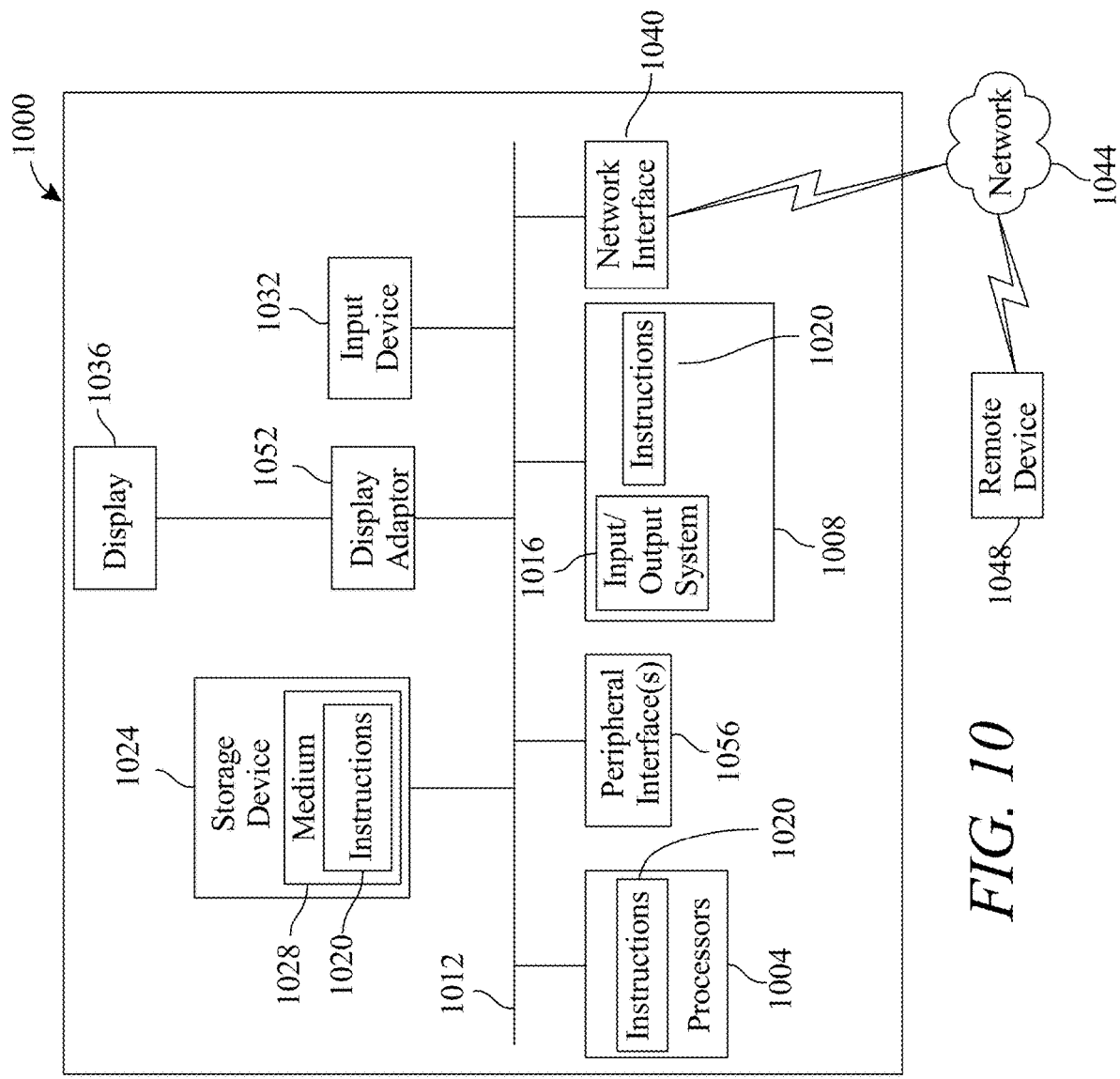
FIG. 10 is a block diagram of a computing system that can be used to implement any one or more of the methodologies disclosed herein and any one or more portions thereof.

FIG. 10 shows a diagrammatic representation of one embodiment of a computing device in the exemplary form of a computer system 1000 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1000 includes a processor 1004 and a memory 1008 that communicate with each other, and with other components, via a bus 1012. Bus 1012 may include any of several types of bus structures including, but not limited to, a memory bus, a memory controller, a peripheral bus, a local bus, and any combinations thereof, using any of a variety of bus architectures.

Processor 1004 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1004 may be organized according to Von Neumann and/or Harvard architecture as a non-limiting example. Processor 1004 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating-point unit (FPU), and/or system on a chip (SoC).

Memory 1008 may include various components (e.g., machine-readable media) including, but not limited to, a random-access memory component, a read only component, and any combinations thereof. In one example, a basic input/output system 1016 (BIOS), including basic routines that help to transfer information between elements within computer system 1000, such as during start-up, may be stored in memory 1008. Memory 1008 may also include (e.g., stored on one or more machine-readable media) instructions (e.g., software) 1020 embodying any one or more of the aspects and/or methodologies of the present disclosure. In another example, memory 1008 may further include any number of program modules including, but not limited to, an operating system, one or more application programs, other program modules, program data, and any combinations thereof.

Computer system 1000 may also include a storage device 1024. Examples of a storage device (e.g., storage device 1024) include, but are not limited to, a hard disk drive, a magnetic disk drive, an optical disc drive in combination with an optical medium, a solid-state memory device, and any combinations thereof. Storage device 1024 may be connected to bus 1012 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1024 (or one or more components thereof) may be removably interfaced with computer system 1000 (e.g., via an external port connector (not shown)). Particularly, storage device 1024 and an associated machine-readable medium 1028 may provide nonvolatile and/or volatile storage of machine-readable instructions, data structures, program modules, and/or other data for computer system 1000. In one example, software 1020 may reside, completely or partially, within machine-readable medium 1028. In another example, software 1020 may reside, completely or partially, within processor 1004.

Computer system 1000 may also include an input device 1032. In one example, a user of computer system 1000 may enter commands and/or other information into computer system 1000 via input device 1032. Examples of an input device 1032 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1032 may be interfaced to bus 1012 via any of a variety of interfaces (not shown) including, but not limited to, a serial interface, a parallel interface, a game port, a USB interface, a FIREWIRE interface, a direct interface to bus 1012, and any combinations thereof. Input device 1032 may include a touch screen interface that may be a part of or separate from display 1036, discussed further below. Input device 1032 may be utilized as a user selection device for selecting one or more graphical representations in a graphical interface as described above.

A user may also input commands and/or other information to computer system 1000 via storage device 1024 (e.g., a removable disk drive, a flash drive, etc.) and/or network interface device 1040. A network interface device, such as network interface device 1040, may be utilized for connecting computer system 1000 to one or more of a variety of networks, such as network 1044, and one or more remote devices 1048 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1044, may employ a wired and/or a wireless mode of communication. In general, any network topology may be used. Information (e.g., data, software 1020, etc.) may be communicated to and/or from computer system 1000 via network interface device 1040.

Computer system 1000 may further include a video display adapter 1052 for communicating a displayable image to a display device, such as display device 1036. Examples of a display device include, but are not limited to, a liquid crystal display (LCD), a cathode ray tube (CRT), a plasma display, a light emitting diode (LED) display, and any combinations thereof. Display adapter 1052 and display device 1036 may be utilized in combination with processor 1004 to provide graphical representations of aspects of the present disclosure. In addition to a display device, computer system 1000 may include one or more other peripheral output devices including, but not limited to, an audio speaker, a printer, and any combinations thereof. Such peripheral output devices may be connected to bus 1012 via a peripheral interface 1056. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating a procreant functional program, the system comprising:
   a computing device, the computing device configured to:
   obtain a procreant marker as a function of a procreant system;
   determine a procreant appraisal as a function of the procreant marker, wherein determining further comprises:
   producing a procreant enumeration as a function of the procreant marker; and
   determining the procreant appraisal as a function of the procreant enumeration and a safe range;
   receive a conduct indicator;
   identify a functional signature as a function of the conduct indicator, wherein identifying further comprises:

obtaining a salubrious reference; and identifying the functional signature as a function of the salubrious reference and the conduct indicator using a functional machine-learning model;

training the functional machine-learning model as a function of a functional training set, wherein the functional training set correlates the salubrious reference and the conduct indicator to the functional signature;

update the functional training set as a function of the functional signature;

iteratively train the functional machine-learning model as a function of the updated functional training set; and generate a functional program as a function of the functional signature and procreant appraisal using a program machine-learning model.

2. The system of claim 1, wherein producing the procreant enumeration further comprises identifying a procreant disorder and producing the procreant enumeration as a function of the procreant disorder.

3. The system of claim 1, wherein the conduct indicator includes a dimensional element.

4. The system of claim 1, wherein receiving the conduct indicator further comprises obtaining an exposure element and receiving the conduct indicator as a function of the exposure element.

5. The system of claim 1, wherein identifying the functional signature further comprises:

producing an indicator index as a function of the conduct indicator; and identifying the functional signature as a function of the indicator index.

6. The system of claim 1, wherein identifying the functional signature further comprises determining a root cause and identifying the functional signature as a function of the root cause.

7. The system of claim 1, wherein identifying the functional signature further comprises determining a habit as a function of the conduct indicator and identifying the functional signature as a function of the habit.

8. The system of claim 1, wherein generating the functional program further comprises:

determining a holistic prospect and generating the functional program as a function of the holistic prospect.

9. The system of claim 1, wherein the functional program includes a nourishment program.

10. The system of claim 1, wherein generating the functional program further comprises:

obtaining a procreant functional goal; and generating the functional program as a function of the functional signature and the procreant functional goal using a goal machine-learning model.

11. A method for generating a procreant functional program, the method comprising:

obtaining, by a computing device, a procreant marker as a function of a procreant system;

determining, by the computing device, a procreant appraisal as a function of the procreant marker, wherein determining further comprises;

producing a procreant enumeration as a function of the procreant marker; and determining the procreant appraisal as a function of the procreant enumeration and a safe range;

receiving, by the computing device, a conduct indicator;

identifying, by the computing device, a functional signature as a function of the conduct indicator, wherein identifying further comprises:

obtaining a salubrious reference; and identifying the functional signature as a function of the salubrious reference and the conduct indicator using a functional machine-learning model;

training the functional machine-learning model as a function of a functional training set, wherein the functional training set correlates the salubrious reference and the conduct indicator to the functional signature;

update the functional training set as a function of the functional signature;

iteratively train the functional machine-learning model as a function of the updated functional training set; and generating, by the computing device, a functional program as a function of the functional signature and procreant appraisal using a program machine-learning model.

12. The method of claim 11, wherein producing the procreant enumeration further comprises identifying a procreant disorder and producing the procreant enumeration as a function of the procreant disorder.

13. The method of claim 11, wherein the conduct indicator includes a dimensional element.

14. The method of claim 11, wherein receiving the conduct indicator further comprises obtaining an exposure element and receiving the conduct indicator as a function of the exposure element.

15. The method of claim 11, wherein identifying the functional signature further comprises:

producing an indicator index as a function of the conduct indicator; and identifying the functional signature as a function of the indicator index.

16. The method of claim 11, wherein identifying the functional signature further comprises determining a root cause and identifying the functional signature as a function of the root cause.

17. The method of claim 11, wherein identifying the functional signature further comprises determining a habit as a function of the conduct indicator and identifying the functional signature as a function of the habit.

18. The method of claim 11, wherein generating the functional program further comprises:

determining a holistic prospect and generating the functional program as a function of the holistic prospect.

19. The method of claim 11, wherein the functional program includes a nourishment program.

20. The method of claim 11, wherein generating the functional program further comprises:

obtaining a procreant functional goal; and generating the functional program as a function of the functional signature and the procreant functional goal using a goal machine-learning model.

* * * * *